(12) United States Patent
Srinivasan et al.

(10) Patent No.: US 10,571,439 B2
(45) Date of Patent: Feb. 25, 2020

(54) SUPPRESSOR DEVICE

(71) Applicant: DIONEX CORPORATION, Sunnyvale, CA (US)

(72) Inventors: Kannan Srinivasan, Tracy, CA (US); Glenn M. Kuse, Pleasanton, CA (US); Rong Lin, Santa Clara, CA (US); Sheetal Bhardwaj, Fremont, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 0 days.

(21) Appl. No.: 16/036,548

(22) Filed: Jul. 16, 2018

(65) Prior Publication Data
US 2018/0321197 A1    Nov. 8, 2018

Related U.S. Application Data

(63) Continuation of application No. 13/674,738, filed on Nov. 12, 2012, now Pat. No. 10,048,233.

(51) Int. Cl.
*G01N 30/02* (2006.01)
*G01N 30/92* (2006.01)
(Continued)

(52) U.S. Cl.
CPC .......... *G01N 30/02* (2013.01); *G01N 30/92* (2013.01); *G01N 30/96* (2013.01); *B01D 15/36* (2013.01);
(Continued)

(58) Field of Classification Search
CPC ........ G01N 30/02; G01N 30/92; B01D 15/36; B01D 15/367; B29K 2071/00
See application file for complete search history.

(56) References Cited

U.S. PATENT DOCUMENTS

| 4,265,634 A | 5/1981 | Pohl |
| 4,290,775 A | 9/1981 | Stevens et al. |
| (Continued) | | |

FOREIGN PATENT DOCUMENTS

| CN | 1403811 | 3/2003 |
| CN | 1744945 | 3/2006 |
| (Continued) | | |

OTHER PUBLICATIONS

Dionex Column Product Manual for IonPac AS22 IonPac AS22-Fast, Doc No. 065119-08, Mar. 2013, 63 pages.
(Continued)

*Primary Examiner* — Dennis White
*Assistant Examiner* — Bryan Kilpatrick

(57) ABSTRACT

An apparatus for detecting analytes in a liquid sample may include an elongated primary channel through which an ionic species flows, the primary channel extending through a primary channel member, a first regenerant channel through which a regenerant flows, the first regenerant channel extending adjacent to the primary channel and being formed in a first block, a first charged barrier having exchangeable ions capable of passing ions of only one charge, positive or negative, and of blocking bulk liquid flow, the first charged barrier disposed between the primary channel member and the first block for separating the primary channel from the first regenerant channel, and a first sealing member disposed between the first charged barrier and the first block defining the first regenerant channel.

14 Claims, 19 Drawing Sheets

(51) Int. Cl.
  *G01N 30/96* (2006.01)
  *B01D 15/36* (2006.01)
  *B29K 71/00* (2006.01)

(52) U.S. Cl.
  CPC ........ *B01D 15/367* (2013.01); *B29K 2071/00* (2013.01)

(56) References Cited

U.S. PATENT DOCUMENTS

| | | | |
|---|---|---|---|
| 4,474,664 | A | 10/1984 | Stevens et al. |
| 4,751,189 | A | 6/1988 | Rocklin |
| 4,999,098 | A | 3/1991 | Pohl et al. |
| 5,045,204 | A | 9/1991 | Dasgupta et al. |
| 5,248,246 | A | 9/1993 | Lew et al. |
| 5,248,426 | A | 9/1993 | Stillian et al. |
| 5,352,360 | A | 10/1994 | Stillian et al. |
| 5,518,622 | A | 5/1996 | Stillian et al. |
| 5,569,365 | A | 10/1996 | Rabin et al. |
| 5,597,481 | A | 1/1997 | Stillian et al. |
| 5,597,734 | A | 1/1997 | Small et al. |
| 5,773,615 | A | 6/1998 | Small et al. |
| 5,788,826 | A | 8/1998 | Nyberg |
| 5,935,443 | A | 8/1999 | Anderson, Jr. et al. |
| 6,077,434 | A | 6/2000 | Srinivasan et al. |
| 6,325,976 | B1 | 12/2001 | Small et al. |
| 6,328,885 | B1 | 12/2001 | Srinivasan et al. |
| 6,331,250 | B1 | 12/2001 | Kaneko et al. |
| 6,425,284 | B1 | 7/2002 | Srinivasan et al. |
| 6,436,719 | B1 | 8/2002 | Srinivasan et al. |
| 6,495,371 | B2 | 12/2002 | Small et al. |
| 6,508,985 | B2 | 1/2003 | Small et al. |
| 6,610,546 | B1 | 8/2003 | Liu et al. |
| 7,399,415 | B2 | 7/2008 | Srinivasan et al. |
| 7,473,354 | B2 | 1/2009 | Liu et al. |
| 7,517,696 | B2 | 4/2009 | Srinivasan et al. |
| 7,524,457 | B2 | 4/2009 | Srinivasan et al. |
| 8,216,515 | B2 | 7/2012 | Liu et al. |
| 8,333,891 | B2 | 12/2012 | Wyatt |
| 8,415,168 | B2 | 4/2013 | Liu et al. |
| 10,048,233 | B2 * | 8/2018 | Srinivasan ............. G01N 30/02 |
| 2005/0034997 | A1 | 2/2005 | Dimascio et al. |
| 2005/0258360 | A1 | 11/2005 | Whitehouse et al. |
| 2006/0057733 | A1 | 3/2006 | Liu et al. |
| 2006/0186046 | A1 | 8/2006 | Liu et al. |
| 2006/0254969 | A1 | 11/2006 | Yamanaka et al. |
| 2007/0051684 | A1 | 3/2007 | Grebenyuk et al. |
| 2007/0062873 | A1 | 3/2007 | Liu et al. |
| 2008/0053830 | A1 | 3/2008 | Tsonev et al. |
| 2008/0314750 | A1 | 12/2008 | Hagner-McWhirter et al. |
| 2009/0127200 | A1 | 5/2009 | Dasgupta et al. |
| 2009/0166293 | A1 | 7/2009 | Srinivasan et al. |
| 2009/0308757 | A1 | 12/2009 | Crettenand |
| 2013/0306565 | A1 | 11/2013 | Davis |
| 2014/0134050 | A1 | 5/2014 | Srinivasan et al. |
| 2014/0332387 | A1 | 11/2014 | Srinivasan et al. |

FOREIGN PATENT DOCUMENTS

| | | |
|---|---|---|
| CN | 101952717 A | 1/2011 |
| CN | 103969378 A | 8/2014 |
| EP | 0032770 B1 | 6/1984 |
| EP | 0180321 B1 | 2/1991 |
| EP | 0442224 A2 | 8/1991 |
| EP | 0555962 A2 | 8/1993 |
| EP | 2390660 A1 | 11/2011 |
| JP | H05281215 A | 10/1993 |
| JP | H07308548 A | 11/1995 |
| JP | 2002535618 A | 10/2002 |
| JP | 2009509139 A | 3/2009 |
| JP | 2013195301 A | 9/2013 |
| JP | 5562247 B2 | 7/2014 |
| KR | 100442020 B1 | 7/2004 |
| WO | 2004070377 A2 | 8/2004 |
| WO | WO2006034182 A1 | 3/2006 |
| WO | 2008024500 A2 | 2/2008 |
| WO | WO2012074455 A1 | 6/2012 |

OTHER PUBLICATIONS

Dionex Column Product Manual for IonPac AS23, Doc No. 065120-06, May 2013, 51 pages.

Dionex Column Product Manual IonPac AS15, Document No. 031362-10, Jun. 2014, 60 pages.

Dionex Product Manual ASRS(R) 300 CSRS(R) 300, Document No. 031956, Rev. 05, Aug. 2007, 51 pages.

Dionex Product Manual for ERS 500 Suppressor, Doc No. 031956-09, Nov. 2013, 69 pages.

Dionex Product Manual for IonPac(R) CG12A IonPac(R) CS12A, Doc No. 031132, Rev. 09, May 2010, 78 pages.

Dionex Product Manual IonPac AS18 Fast, Document No. 031878-08, Jun. 2012, 54 pages.

Douglas et al., "New suppressor technology improve trace level anion analysis with carbonate-hydrogencarbonate mobile phases," J Chrom A, 956, 2002, 47-51.

Saari-Nordhaus et al., "Recent advances in ion chromatography suppressor improve anion separation and detection," J Chrom A, 956 (2002) 15-22.

Srinivasan et a., "Suppressor Design and Detection for Ion Chromatography" in: "Applications of Ion chromatography for Pharmaceutical and Biological Products," Mar. 9, 2012, John Wiley & Sons, Inc., pp. 91-105.

U.S. Appl. No. 13/674,738, filed Nov. 12, 2012, to Srinivasan (specification, claims, abstract only).

* cited by examiner

SUPPRESSOR DEVICE

CROSS-REFERENCE TO RELATED APPLICATION

This application is a Continuation under 35 U.S.C. § 120 and claims the priority benefit of co-pending U.S. Non-Provisional application Ser. No. 13/674,738, filed on Nov. 12, 2012, entitled "SUPPRESSOR DEVICE," the entire disclosure of which is incorporated by reference.

FIELD OF THE INVENTION

The present invention generally relates to an apparatus for separating ionic species in chromatography, and more specifically to a suppressor for suppression of eluents used in the analysis of anions or cations in ion chromatography, or to a sample pre-treatment device for removing interfering anions or cations from the sample before the chromatographic separation.

BACKGROUND OF THE INVENTION

Ion chromatography is widely used in the analysis of samples containing anions or cations. A typical process begins with introducing a sample in the solution of a conductive eluent, and then sequentially goes through chromatographically separating sample ions in the eluent, suppressing the eluent to remove the electrolyte counter ions to the sample ions, and detecting the sample ions. The purpose of suppression is to reduce the background conductivity of the eluent and increase the conductivity of the analytes, thus increasing the response in the subsequent detection.

Various suppressors are known and can be used for suppressing the eluent. Examples include those disclosed in U.S. Pat. Nos. 4,999,098, 6,328,885 and 7,618,826. In these suppressors, suppression is achieved by flowing the eluent through an eluent channel and a regenerant through a regenerant channel, where the eluent channel is separated from the regenerant channel by a charged membrane. The eluent and regenerant channels are defined by gaskets and rely on the gaskets for liquid-tight seal. Similarly, U.S. Pat. No. 6,752,927 discloses a salt converter device that uses gasketed screens and U.S. Pat. No. 6,808,608 discloses water purification devices that use gasketed screens. The gaskets are typically made of elastomeric materials, such as polyurethane or flexible liquid silicone-based rubber, set in place by press or UV initiated curing process.

Under certain circumstances such as an extreme pressure or temperature or upon long term usage, using gaskets to define and seal the eluent and regenerant channels may adversely affect the life time of these devices and in some instances chromatographic performance such as backpressure, noise performance, and peak band dispersion. For example, as the elastomeric gasket is compressed for seal, the overall forces tend to squeeze the gasket outward into the open area, for example, eluent and regenerant channels, over time. In some cases, such change generates significant backpressure and clogging in fluidic channels and causes leakage. In some cases, the gaskets are thinned out significantly due to the compression forces and no gasket is available in place to make a proper seal. Further, the force per unit area decreases over time as the gasket material is compressed, requiring significant torque optimization to overcome such change. In addition, exposure to higher temperatures may result in higher levels of leachates or melting of the gaskets which affects the noise performance or flow properties and in some cases may irreversibly damage the suppressors. Prior art devices also have the gasket as an integral part of the screen (i.e., gasketed screen) where the screen area is at least slightly larger than the channel and partially embedded into the gasket. This means that the access of the eluent to some areas of the screens is slow due to diffusion limitations. For example, the area close to the gasket edge defining the eluent channel fluidic pathway exhibits this diffusional limitation. The net effect of this behavior is that when the screen form is changed from one form to another (e.g., hydronium form to sodium form) there is slow diffusion of the reagents from within the gasketed screen to an open area away from the gasket edge. In another example when a cation exchange screen gasket was exposed to base eluent without any power applied to the suppressor the screen gets converted to the sodium form. There can be slow diffusion of sodium into the screen area located underneath the gasket proximate to the gasket edge. Upon resuming normal operation the peak area remains small until all of the sodium diffuses out of the gasketed region of the eluent channel. This is a slow process. In other instances when pursuing a high to low ratio of analyte analysis the slow diffusion of analyte can cause peak shape issues. Although many of the above problems could be circumvented by operating in a narrow operational regime in terms of pressure, temperature, concentration this imposes constraints from an operational perspective.

Conventional suppressors may have other limitations. For example, conventional suppressors incorporate fluidic geometries having different areas for the regenerant and eluent channels, thus the sealing across the channels are not uniform. Further, conventional suppressors incorporate a fluidic pathway design that routes eluent flow to the eluent channel via the regenerant gasket. This imposes the need to align the inlet and outlet of the eluent flow gasket with the through holes of the regenerant gasket during assembly and maintain the alignment over time. A slight alignment offset can result in high backpressure as well as poor peak shapes In light of the above, it is desirable to provide improved devices that overcome at least some of the above-mentioned challenges of devices that use gasketed screens.

The information disclosed in this Background section is only for enhancement of understanding of the general background of the invention and should not be taken as an acknowledgement or any form of suggestion that this information forms the prior art already known to a person skilled in the art.

SUMMARY

Various aspects of the present invention provide for an apparatus for use in detecting analytes in a liquid sample. The apparatus may include a primary channel through which an ionic species flows, the primary channel extending through a primary channel member, a first regenerant channel through which a regenerant flows, the first regenerant channel extending adjacent to the primary channel and being formed in a first block, a first charged barrier having exchangeable ions capable of passing ions of only one charge, positive or negative, and of blocking bulk liquid flow, the first charged barrier disposed between the primary channel member and the first block for separating the primary channel from the first regenerant channel, and a first sealing member disposed against the first charged barrier for sealing at least one of the primary channel member and the first regenerant channel.

The primary channel member may be a plate or a sheet. The primary channel member may preferably be formed of polyether ether ketone (PEEK).

The first block may include a shelf for positioning the first sealing member on the first block and the first sealing member may define a peripheral shape of the first regenerant channel. The shelf may partially define a groove that receives the first sealing member therein.

The first block may be formed of a polymer. The first block may preferably be formed of PEEK.

The first sealing member may be formed of a material selected from the group consisting of ethylene propylene diene monomer (EPDM) rubbers, thermoplastic elastomers, polypropylene, polytetrafluoroethylene (PTFE), and combinations thereof.

The first regenerant channel may be configured to have a substantially hexagonal shape. The first regenerant channel may be configured to include a fluidic area that substantially matches a fluidic area of the primary channel.

The ionic species of the eluent include ions or compounds of molecules having high ionic strength.

The eluent may flow through the primary channel in a first direction and the regenerant may flow through the first regenerant channel in a second direction that is substantially opposite to the first direction. The primary channel member, the first charged barrier and the first block may include coaxial holes for facilitating alignment of the first charged barrier respective to the regenerant channel.

The apparatus may further include a first screen for enhancing ion exchange and/or mixing, the first screen disposed within the first regenerant channel. The apparatus may further include a second regenerant channel extending adjacent to the primary channel and being formed in a second block, a second charged barrier having exchangeable ions capable of passing ions of only one charge, positive or negative, and of blocking bulk liquid flow, the second charged barrier disposed between the primary channel member and the second block for separating the primary channel from the second regenerant channel, and a second sealing member disposed against the second charged barrier for sealing at least one of the primary channel member and the second regenerant channel.

The primary channel may include an eluent inlet at one end and with an eluent outlet at the other end thereof, the first regenerant channel includes a first regenerant inlet at one end and with a first regenerant outlet at the other end thereof. The second regenerant channel may include a second regenerant inlet at one end and with a second regenerant outlet at the other end thereof. The eluent inlet and the eluent outlet may be independent from the first regenerant inlet and the first regenerant outlet and from the second regenerant inlet and the second regenerant outlet. The independent flowing ionic species flows through the eluent inlet and outlet without touching the first or second block.

The apparatus may further include first and second electrodes in electrical communication with the first regenerant channel and the second regenerant channel, respectively, for enhancing ionic transport between the primary channel and the regenerant channels. The apparatus may further include first and second external blocks for structurally supporting the apparatus.

Other aspects of the present invention provide for an ion chromatography system to detect analytes in a liquid sample. The ion chromatography system may include a separation column, the apparatus that is in fluidic communication with the separation column to receive an eluted liquid from the separation column, and a detector in fluidic communication with the apparatus to detect desired ions in the eluted fluid from the apparatus. The ion chromatography system may further include a pump to move liquid from a reservoir, and a sample injection device to introduce a sample in the eluent, wherein the sample injection device is in fluidic communication with the separation column for delivering the eluent with the sample to the separation column.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

Like reference numerals refer to corresponding parts throughout the several views of the drawings.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
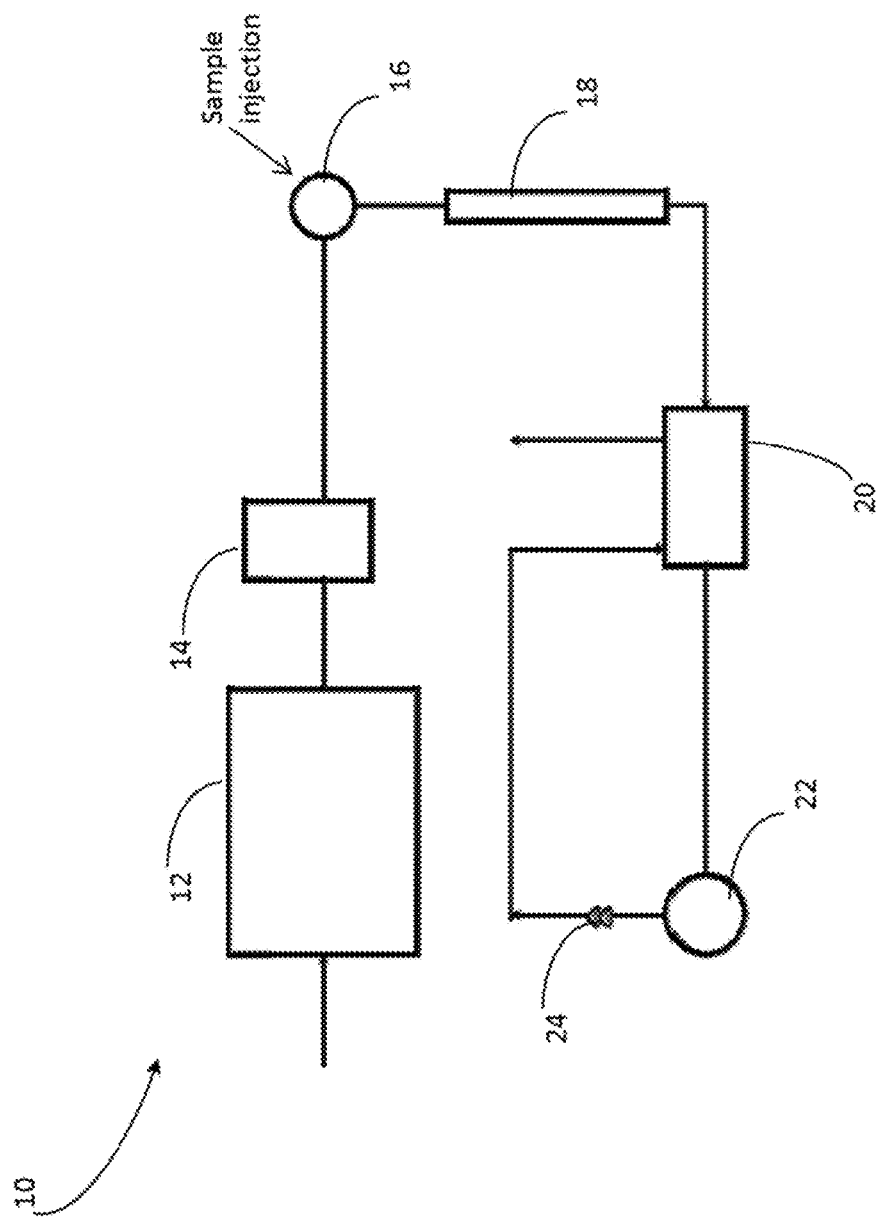
FIG. 1 illustrates a system for performing ion chromatography in which an exemplary suppressor in accordance with the present application is used.

Referring to FIG. 1, there is depicted an ion chromatography (IC) system 10 for the analysis of anions or cations in ion chromatography, which is useful for determining a large number of ionic species so long as the species to be determined are solely anions or solely cations. Herein, the term "ionic species" refers to species in ionic form and components of molecules having high ionic strength which are ionizable under the conditions of the present system. The eluent may also comprise of solvents such as methanol, acetonitrile, isopropanol and the like. The system 10 in general includes components for eluent generation, sample injection, ion-exchange separation, suppression or ionic detection. The system 10 may also include data acquisition or control devices.

As an example, FIG. 1 illustrates the eluent generation from deionized water drawn by a pump 12 and delivered to an eluent generator 14. The eluent generator 14 may be of any suitable type, including those manufactured by Thermo Scientific (Sunnyvale, Calif., USA) such as EGC, EG40 and EG50. The eluent generator 14 may be used in combination with other components, such as continuously regenerated trap columns (CR-TC) or high pressure degas assembly manufactured by Dionex. The generated eluent is electrically conductive. With the presence of a CR-TC column or degas assembly, the generated eluent flows through the CR-TC column and into the high pressure degas assembly. Alternatively, the eluent may be prepared manually and drawn from an eluent reservoir (not shown) using a high-pressure pump 12. In this case there is no need for an eluent generator 14.

A suitable sample is then introduced, for example, through a sample injection valve 16, and flows in the solution of the eluent into chromatographic separation means, typically in the form of a chromatographic column 18 which is packed with a chromatographic separation medium. The separation medium may be in the form of ion-exchange resin, monolith or a porous hydrophobic chromatographic resin with essentially no permanently attached ion-exchange sites.

The solution leaving the column 18 is directed to suppression means typically in the form of a suppressor 20 arranged in series with the column 18. The suppressor 20 suppresses the conductivity of the electrolyte of the eluent from column 18 but not the conductivity of the separated ions. The conductivity of the separated ions is usually enhanced in the suppression process. For instance, an exemplary anion Cl$^-$ can be enhanced by converting it to the acid form HCl. After passing through the suppressor 20, the eluent is neutralized to produce its weakly ionized form. For instance, the exemplary eluent OH$^-$ can be neutralized by reacting it with hydronium ion to form water. Typically, the suppressor 20 includes a primary channel through which an ionic species flows and a regenerant channel through which a regenerant flows. One will appreciate that the device may be used for IC suppression as well as sample pre-treatment and other uses, and as such, the primary channel may direct an eluent with an ionic species flow, or alternatively, may simply direct a liquid including an ionic species. The suppressor 20 will be described in detail hereinafter.

The suppressed eluent is then directed to detection means typically in the form of a conductivity cell 22 for detecting the resolved ionic species. In conductivity cell 22, the presence of ionic species produces an electrical signal proportional to the amount of ionic material. Such signal is typically directed from the cell 22 to a conductivity meter, thus permitting detection of the concentration of separated ionic species. The conductivity cell 22 may be electrically connected to devices such as a computer or data acquisition system for acquiring and processing the data or controlling the system.

After passing through the conductivity cell 22, the eluent may be redirected to the regenerant channel on the suppressor 20, thus providing a source of water to the suppressor 20 and eliminating a need for an external supply of water similar to what is described in U.S. Pat. No. 5,352,360, the entire content of which is incorporated herein for all purposes by this reference. The suppressed eluent may be directed to waste or other devices to provide water or remove components such as gases. To prevent the eluent in the conductivity cell 22 from out-gassing, the system 10 may include a back pressure coil or back pressure coils 24, through which the eluent flows before redirecting to the regenerant channel on the suppressor 20. The back pressure coil or coils 24 help to prevent gases, generated during suppression, from out-gassing and prevent formation of bubbles in the conductivity cell 22, thus reducing the noises and improving the accuracy of the detection.

Figure 2:
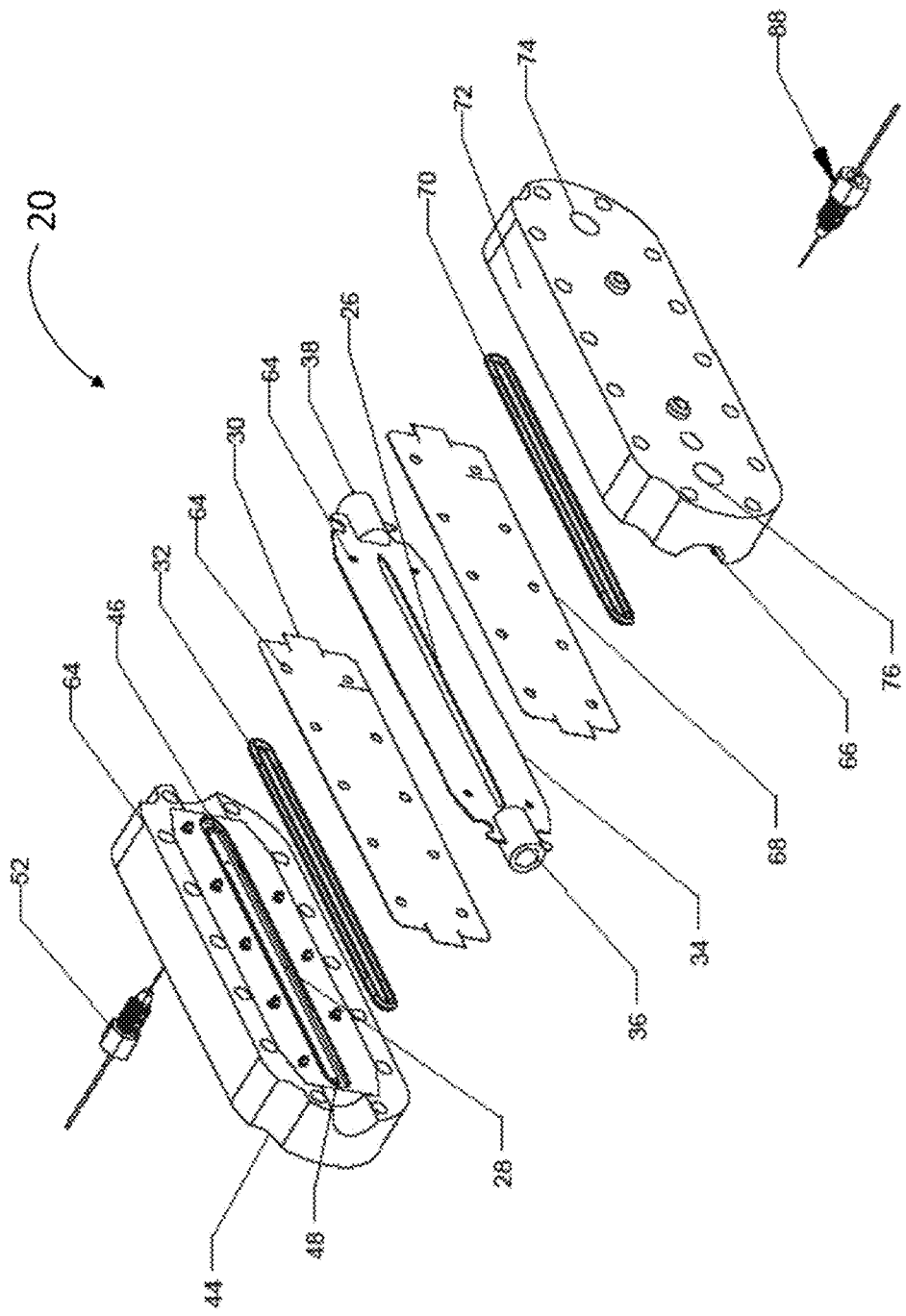
FIG. 2 illustrates an exploded perspective view of an exemplary suppressor in accordance with the present application.

Referring now to FIG. 2, there is depicted an exploded exemplary suppressor 20 including a primary or eluent channel 26, a first regenerant channel 28, a first charged barrier 30 and a first sealing member 32. Unlike conventional suppressors where eluent and regenerant channels are defined and sealed by gasketed screens, the eluent channel 26 of the present application is formed in a first eluent channel member 34 and the first regenerant channel 28 is formed on a first block 44 that is typically disposed on a side of the eluent channel member 34. The first charged barrier 30 is disposed between the eluent channel member 34 and the first block 44 and separates the eluent channel 26 from the first regenerant channel 28. The first sealing member 32 can be disposed against the first charged barrier 30 for sealing one of the eluent channel member 34 and the first regenerant channel 28. As illustrated in FIG. 2, the first sealing member 32 directly forms the seal to the first regenerant channel 28 and indirectly forms the seal to the eluent channel 26 by urging the first charged barrier 30 against the eluent channel member 34. The first sealing member 32 is disposed between the first charged barrier 30 and the first block 44. The first sealing member 32 partially defines the first regenerant channel 28 and provides a liquid-tight seal to the eluent channel 26 and the first regenerant channel 28. One will appreciate that in various embodiments, the suppressor may be configured with a sealing member utilized to form an eluent channel between the charged barrier and the eluent channel plate, and a regenerant channel defined by the compartment in the first block and enclosed with the other side of the first charged barrier. The function of the sealing member is to seal between the eluent channel member and the first block via the first charged barrier.

Figure 3A:
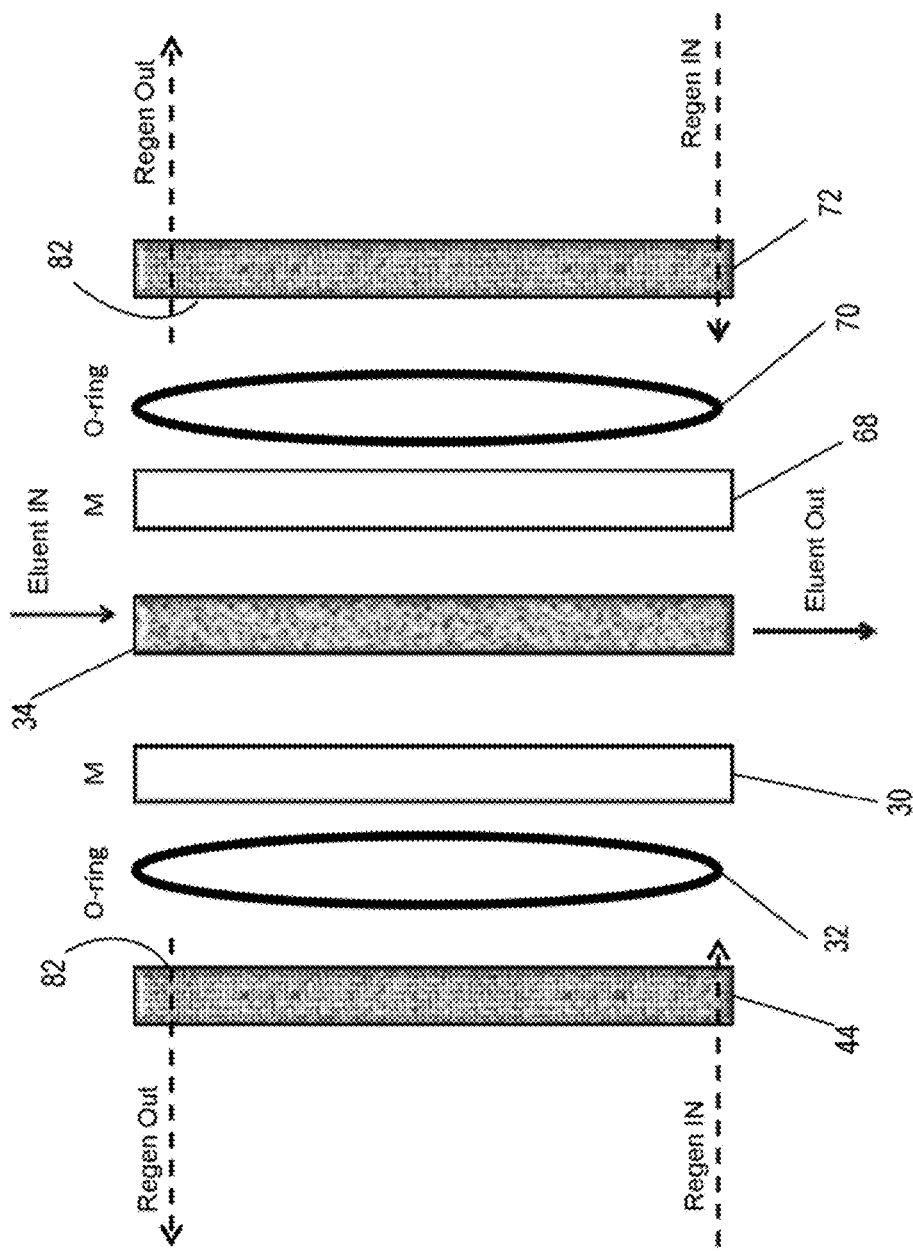
FIG. 3A illustrates a schematic of the placement of a first sealing member that is in between the first block and the first charged barrier, and a second sealing member in between the second block and the second charged barrier in accordance with the present application.

FIG. 3A illustrates a side view schematic where the first sealing member 32 is in between the first block 44 and the first charged barrier 30 and the second sealing member 70 is in between the second block 72 and the second charged barrier 68. In this configuration, the sealing members 32 and 70 directly form the seal to the first and second regenerant channels within the first and second blocks 44 and 72, respectively, and indirectly form the seal to the eluent channel 26 by urging the first and second charged barrier 30 and 68 against the eluent channel member 34, which is in accordance with the configuration of FIG. 2.

Figure 3B:
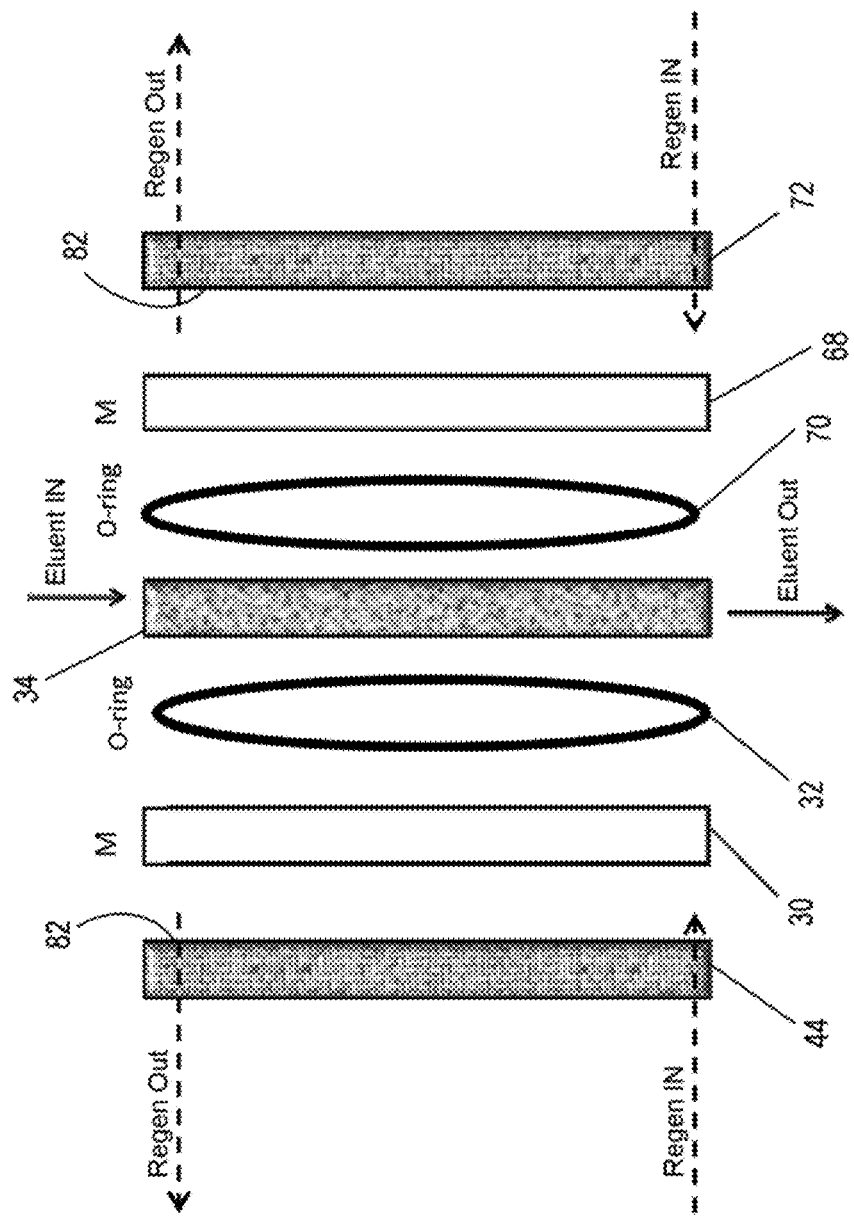
FIG. 3B illustrates a schematic of the placement of a first sealing member that is in between the first charged barrier and the primary channel member, and a second sealing member in between the second charged barrier and the primary channel member in accordance with the present application.

FIG. 3B illustrates a side view schematic where the first sealing member 32 is in between the eluent channel member 34 and the first charged barrier 30 and the second sealing member 70 is in between the eluent channel member 34 and the second charged barrier 68. In this configuration the sealing member 32 and 70 directly forms the seal to the eluent channel member 34 and indirectly forms the seal to the first and second regenerant channels within the first and second blocks 44 and 72, respectively, by urging the first and second charged barrier 30 and 68 against the first and second regenerant channel, respectively. It should be noted that portions of the first and second sealing members, proximate to the inlet and outlet of the eluent channel member 34, may have a detail, a notch, or a recess so that fluid can flow through the eluent channel. In an embodiment, the eluent channel member may have a groove on both sides to help align and seat the first and second sealing members. In another embodiment, the first and second sealing members may be aligned manually and then held in place by the force used to form the assembled sandwich structure. Thus, as illustrated in FIGS. 3A and 3B, each sealing member helps seal two channels in accordance with the present invention.

In yet another configuration (not shown), the sealing members 32 and 70 can be replaced with a single sealing member which is disposed in the eluent channel member 34. The sealing member is located along the perimeter of the eluent channel. The sealing member has a height that is greater than the eluent channel member and thus protrudes outwardly to contact the first and second charged barriers. By urging the first and second charged barriers 30 and 68 against the first and second regenerant channels 28 and 66, a seal is formed. In the above configuration, one sealing member is used to seal three channels.

In still yet another configuration (not shown), the sealing members 32 and 70 can be replaced with a monolithic part that integrates the eluent channel member 34 and two sealing members together. The monolithic part is formed with the shape of the eluent channel member 34 with the two sealing members already affixed thereon. This design provides a simpler design in that the assembly process does not require the manufacturing placement and alignment of the two sealing members. Similar to the above embodiments, the sealing member portions proximate to the inlet and outlet of the eluent channel member 34 may have a detail, a notch, or a recess so that fluid can flow through the eluent channel.

Figure 4:
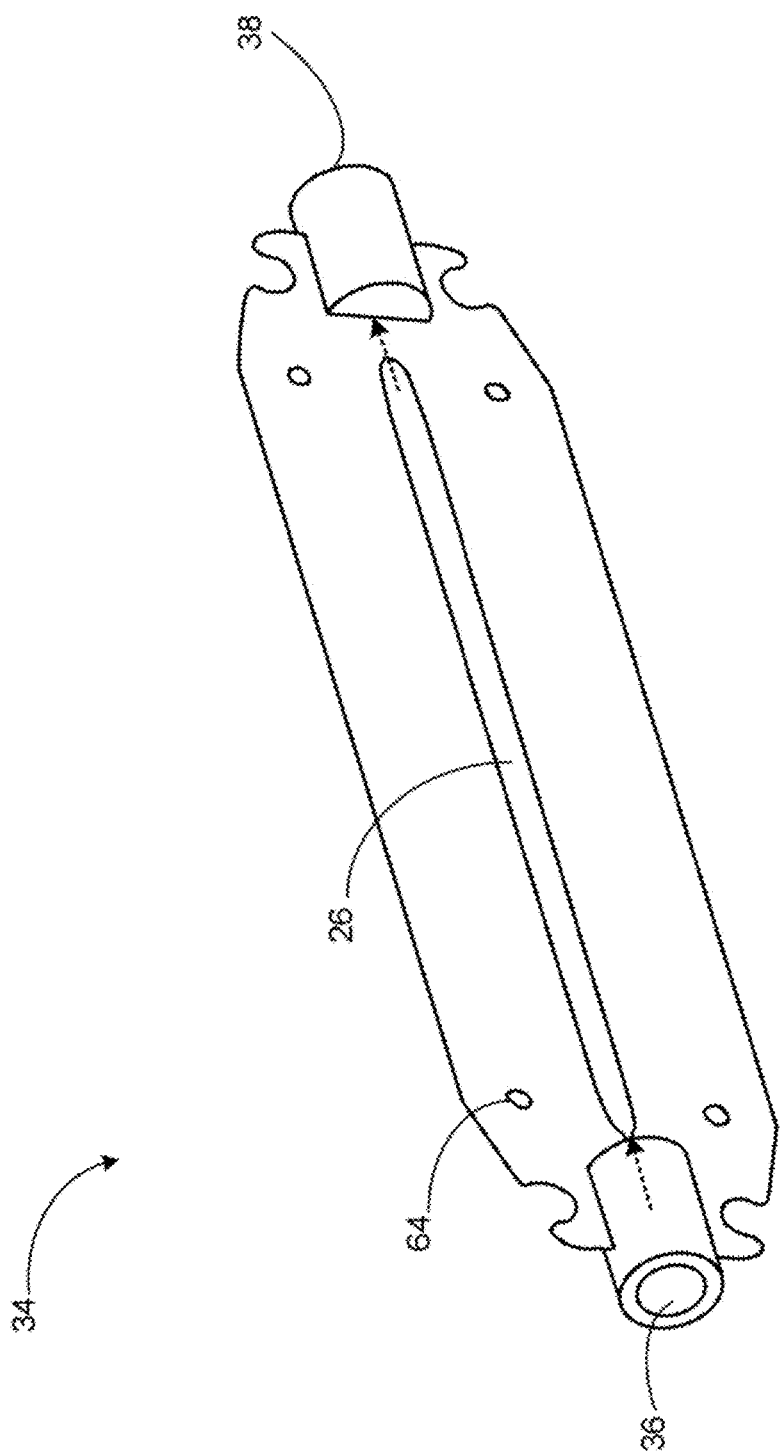
FIG. 4 illustrates an exemplary eluent channel formed in a plate in accordance with the present application.

The eluent channel 26 may extend through the eluent channel member 34 typically in the form of a plate or a sheet, and have an eluent inlet 36 at one end and an eluent outlet 38 at the other end of the eluent channel 26. An exemplary eluent channel formed in a plate 34 is illustrated in FIG. 4. Plate 34 can include two side edges, a first end edge, and a second end edge. The two side edges run approximately parallel to the flow of the eluent channel. As illustrated in FIG. 4, plate 34 can also include a top and bottom surface where the channel area 26 traverses through the plate from the top surface to the bottom surface. The eluent inlet 36 and the eluent outlet 38 may be ports having substantially cylindrical shape and may be coupled with or monolithically formed with the eluent channel member 34. Eluent inlet 36 may be at least partially formed by a hole (not shown) drilled into a first end edge of plate 34 that bridges across to eluent channel 26. Note that the drilled holes at the end edges run along an axis substantially parallel to the eluent channel 26. Similarly, eluent outlet 38 may be at least partially formed by a hole (not shown) drilled into a second end edge of plate 34 that bridges across to eluent channel 26. As illustrated in FIG. 4, the first end edge and the second end edge are disposed on substantially opposed ends of plate 34 proximate to eluent inlet 36 and eluent outlet 38, respectively. In an embodiment, plate 34 may have a height of 0.01 inches with a drilled hole at both end edges having a diameter of 0.005 inches. As such, fluid can independently flow through the eluent inlet and outlet without touching the first or second block. It is also feasible to attach tubings to the channel member 34 where the tubing partially defines the eluent inlet and outlet to the eluent channel 26. In this case, the cylindrical housing adapters that are attached to the eluent channel member, as illustrated in FIG. 4, can be eliminated. In various embodiments, the eluent channel 26 may be elongated along the direction of the eluent flow and optimized to reduce or eliminate the dead volume for minimizing the peak band dispersion. In various embodiments, the inlet is on a port face that communicates to the fluidic pathway or open area 26 via a channel or conduit. By way of illustration, FIG. 4 depicts the first eluent channel member 34 comprising a single plate or sheet. It should be noted that the first eluent channel member 34 may comprise a plurality of plates or sheets which collectively provide for formation of the eluent channel 26. When used in the system 10, the eluent inlet 36 is fluidically coupled with the column 18 and the eluent outlet 38 is fluidically coupled with the conductivity cell 22. Other detectors/detector cells could be used in place of the conductivity cell 22. Fittings or other fluidic connectors may be used to facilitate the fluidic coupling of the eluent inlet 36 with the column 18 and the eluent outlet 38 with the conductive cell 22, respectively. The eluent channel member 34 may be made of a polymer material such as polyether ether ketone (PEEK) or PVC (polyvinylchloride) or PVDF (Polyvinylidene fluoride) and the like.

The first charged barrier 30, disposed between the eluent channel member 34 and the first block 44, separates the eluent channel 26 from the first regenerant channel 28. Typically, the first charged barrier 30 is in the form of an ion-exchange membrane sheet having exchangeable ions and capable of passing ions of only one charge, positive or negative, and of blocking bulk liquid flow. The first charged barrier 30 may be of a type such as disclosed in U.S. Pat. No. 4,999,098, the disclosure of which is incorporated herein by reference. In particular, such sheets may be cation-exchange or anion-exchange membranes with polyethylene, polypropylene, polyethylene-vinylacetate-based substrates. Other suitable substrates include poly-vinylchloride or polyfluorocarbon-based materials. The substrate polymer is organic solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alkylvinylpyridines. As an example, to form a cation-exchange membrane, the sheets grafted with styrene monomers are functionalized suitably with chlorosulfonic acid, sulfuric acid, or other $SO_2$ or $SO_3$ sources. To form an anion-exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 20 mil thick, and preferably no more than 4-10 mil when wet. Suitable membranes of the foregoing type are provided by RAI Research Corp., Hauppauge, N.Y. (the cation exchange membrane provided under designation R5010 (0.008 inch thick) and the anion-exchange membrane under designation R4015 (0.004 inch thick)). Suitable barriers include ion-exchange membranes sold under the trademark Nafion®. Membranes can also be manufactured from a radiation grafting process using suitable monomers followed by functionalization. It should be noted that the charged membranes could also be of the bipolar type. One or more membranes could form the charged barrier of the present invention.

Figure 5A:
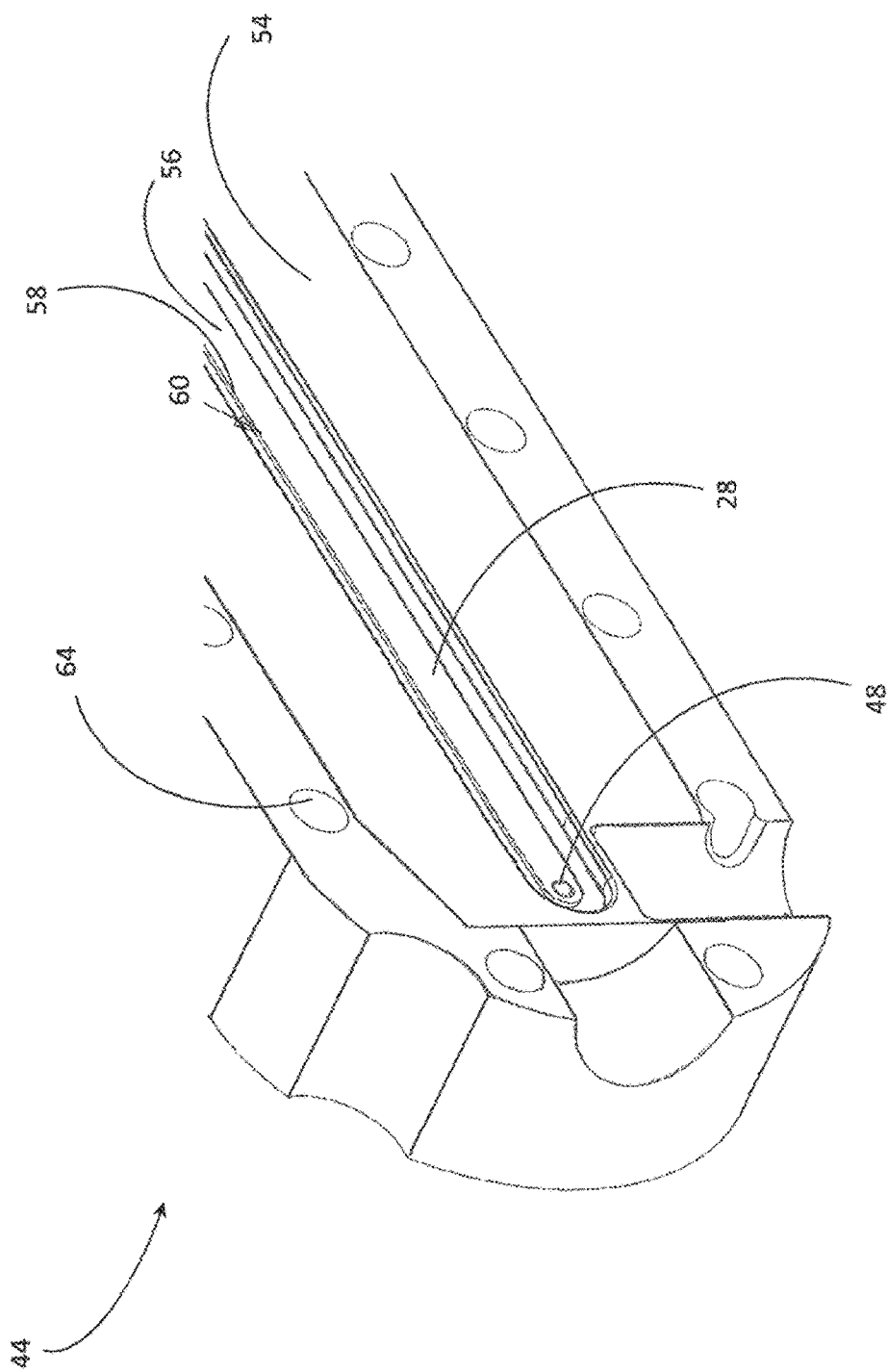
FIGS. 5A-5C illustrate partially enlarged views of an exemplary first block of the suppressor in accordance with the present application.
Figure 5B:
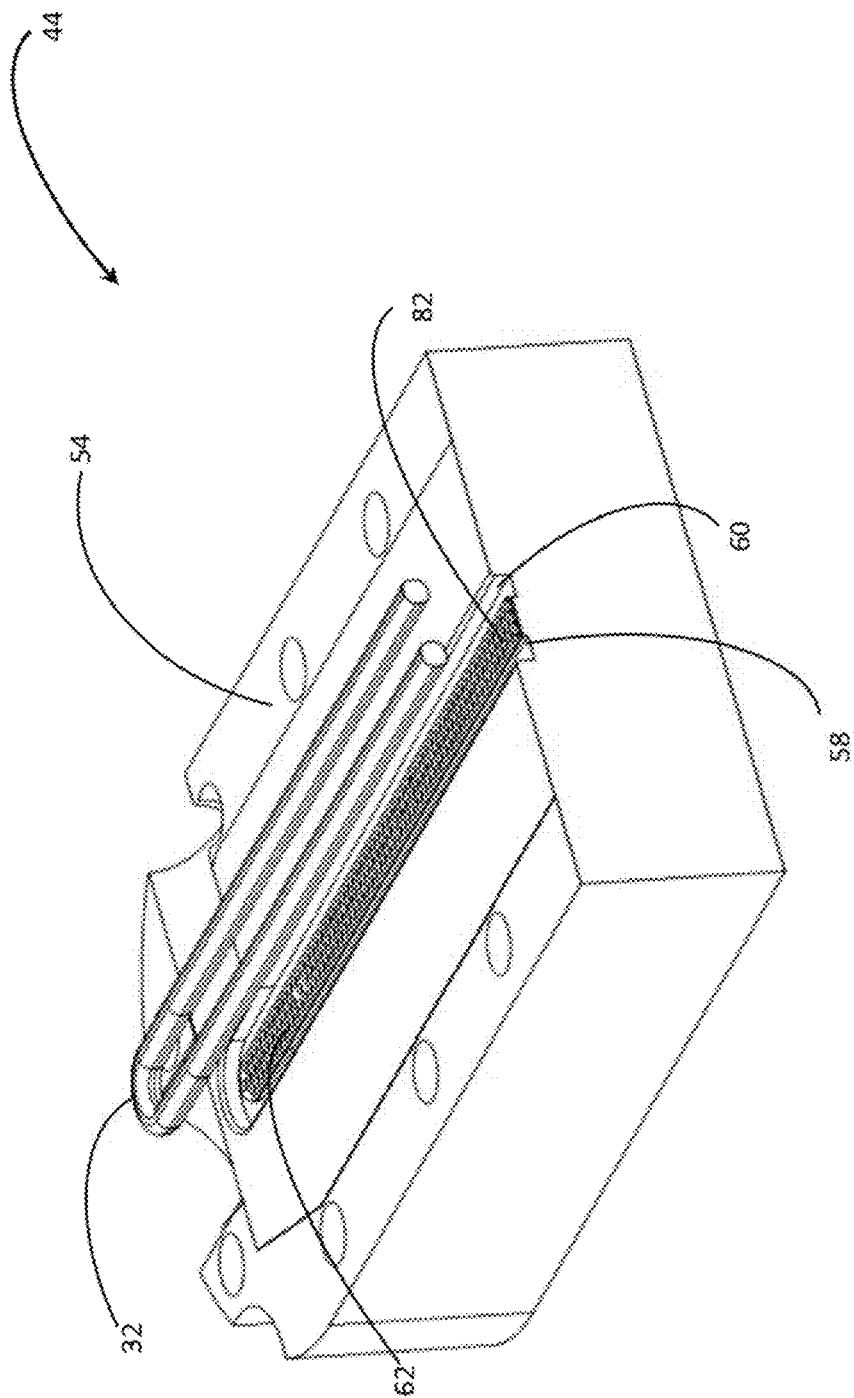
Figure 5C:
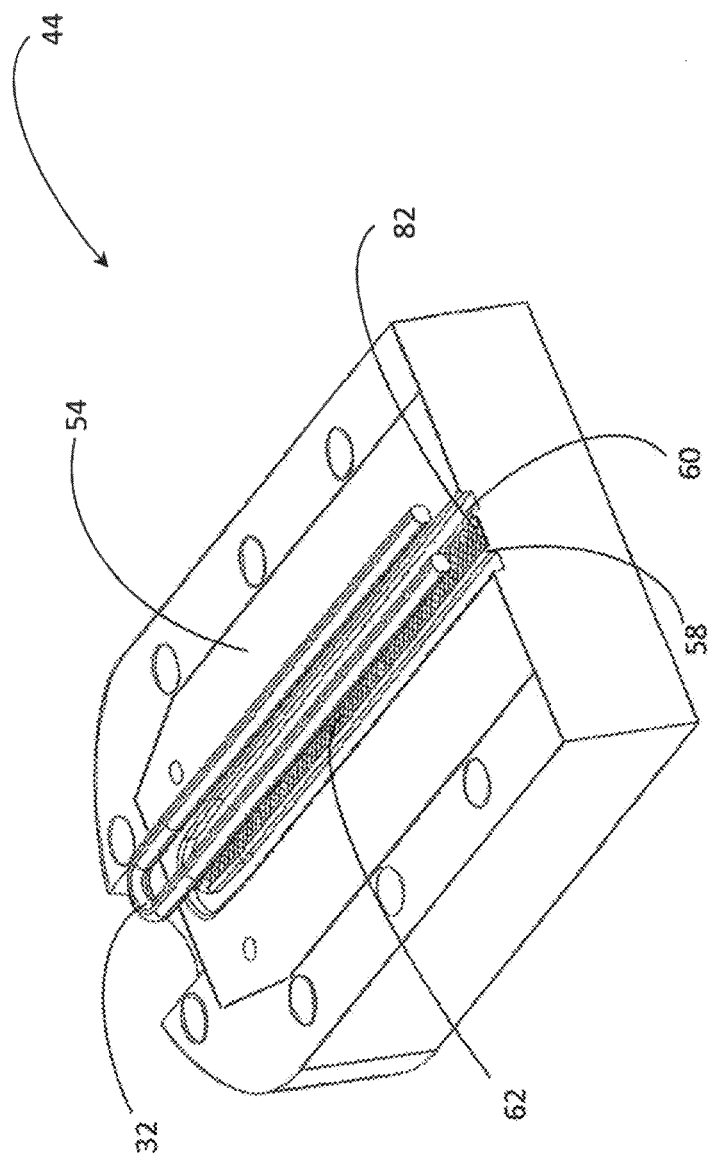

Unlike regenerant channels defined by gasketed screen materials in conventional membrane suppressors, the first regenerant channel 28 of the present application is formed in the first block 44 that is typically made of a hard polymer material such as PEEK. The first block 44 is disposed on one side of the eluent channel member 34, an exemplary configuration of which is illustrated in FIGS. 5A-5C.

As shown, the first block 44 has a flat surface 54 that faces the eluent channel member 34 and a compartment 56 formed substantially in the central part of the first block 44. Within the compartment 56, a shelf or a ledge 58 is protruded from the bottom of the compartment 56, and substantially along the perimeter of the compartment 56. Together with the peripheral wall of the compartment 56, the shelf or ledge 58 forms a groove 60 that receives the first sealing member 32. The first sealing member 32 is may be in the form of an O-ring made of any suitable materials, or other closed loop seal of various profiles.

For example, the first sealing member 32 may be formed of a material selected from the group consisting of ethylene propylene diene monomer (EPDM) rubbers, thermoplastic elastomers, polypropylene, polytetrafluoroethylene (PTFE), and combinations thereof. In various embodiments, the sealing member may have a circular cross-section, such as an O-ring, however, one will appreciate that other suitable cross-sections may be utilized, for example, flat, triangular, rectangular, square, hexagonal or other suitably shaped cross sections. The first sealing member 32 could be punched from a flat sheet of polymer material. In this case the cross section of the sealing member is square or rectangular.

The first sealing member 32 defines the peripheral shape of the first regenerant channel 28 on the first block 44. In various embodiments, the first block 44 and its associated features are configured such that the constructed first regenerant channel 28 is oriented along the direction of the regenerant flow and has a fluidic area essentially matching the fluidic area of the eluent channel 26. Herein, the fluidic area of the first regenerant channel 28 refers to the surface area of the first regenerant channel 28 that faces the eluent channel 26, and the fluid area of the eluent channel 26 refers to the surface area of the eluent channel 26 that faces the first regenerant channel 28. In other words, the geometric area and shape formed by the first sealing member and the eluent channel member are substantially about the same. Matching fluidic areas in the eluent channel 26 and the first regenerant channel 28 has several advantages, which will be described hereinafter. To facilitate good sweep out of the regenerant liquid in the first regenerant channel 28, the constructed first regenerant channel 28 may have a peak or V-shape at both ends. That is, the fluidic area of the first regenerant channel 28 may be substantially hexagonal.

The first regenerant channel 28 has a regenerant inlet 46 at one end and a regenerant outlet 48 at the other end of the first regenerant channel 28. In various embodiments, the regenerant inlet 46 and the regenerant outlet 48 are configured such that the regenerant flows countercurrent to the eluent. That is, the eluent flows through the eluent channel in a first direction and the regenerant flows through the first regenerant channel in a second direction that is substantially opposite to the first direction. When used in the system 10, the regenerant inlet 46 is fluidically coupled with a regenerant reservoir or with the back pressure coil 24 and the regenerant outlet 48 fluidically coupled to waste, eluent generator or other devices that use the regenerant stream. Such fluidic couplings of the inlet 46 and the regenerant outlet 48 may be aided by fittings, or by other suitable fluidic connectors (not shown). It should be noted that the regenerant flow could be routed through the hardware to provide a sequential flow or a split flow design. In the sequential flow, the regenerant flow is routed from one regenerant channel to another. In this mode, the regenerant flows at the same flow rate as the eluent in the recycle mode. In the split flow design, the regenerant flow is split so that the fluids flowing in the regenerant channel are independent of each other. It is also conceivable to use a hybrid mode of operation where the recycled fluid is routed to one regenerant channel while an external source is fed to the other regenerant channel. In some applications, a concurrent flow for the regenerant may be adopted such as for a salt converter application as per U.S. Pat. No. 6,752,927.

While conventional membrane suppressors rely on gasketed screen materials for seal, the suppressor 20 of the present application is sealed by the first sealing member 32 positioned or received in the groove 60. As described above, the groove 60 is constructed by the peripheral wall of the compartment 56 and the shelf or ledge 58. The height of the shelf or ledge 58 may vary depending on the desired sealing pressure, band dispersion or other parameters. In various embodiments, it is substantially as tall as the peripheral wall of the concaved compartment 56 or slightly lower than the peripheral wall of the concaved compartment 56. In the most basic form, there is a chamber that includes a groove along the perimeter of the chamber. The groove accommodates the elastomer seal. The groove may have a small ledge and the height of this ledge can be similar to the chamber or more preferably lower than the height of the chamber. The inner perimeter of the ledge defines the regenerant channel area where suitable materials can be placed such as screens, electrodes, resins etc. A significant feature of the present invention is that it decouples the ion exchange screen materials from the sealing materials. In prior devices the ion exchange screens were gasketed and thus any issues with the gasket materials directly impacted the leak or chromatographic performance of the device. By decoupling the sealing aspect from the ion exchange screens in the present invention the chromatographic performance is preserved.

The charged screen 62 may be formed in a similar or the same manner as disclosed in U.S. Pat. No. 4,999,098, the entire content of which is incorporated herein by reference.

FIGS. 5B and 5C depict two examples with the shelf or ledge 58 at different heights. With a height substantially the same as or slightly lower than the peripheral wall of the concaved compartment 56, the shelf or ledge 58 depicted in FIG. 5C may effectively prevent the first sealing member 32 from being squeezed into the first regenerant channel 28 over time, thus reducing or eliminating potential clogging or blockage of the first regenerant channel 28. The configuration of FIG. 5B is chosen when band dispersion is of concern since there is no unswept delay volume or area between the sealing member and the first barrier. The configuration of FIG. 5C is chosen when band dispersion is of no consequence and a more uniform seal and higher pressure resilience is desired. In both instances, the height of the ledge may be chosen so that the sealing member is in place along the perimeter of the compartment so as to avoid the sealing member moving into channel 28 where it could adversely affect the device sealing and performance. Since the first sealing member 32 of the present application is received in and essentially confined by the groove 60, it will remain at that location providing a seal. Unlike prior art gaskets, sealing member will not be thinned out, at least not significantly, when compressed, and thus provides a proper and substantially uniform seal for suppressors. Moreover, the first sealing member 32 has a relatively smaller sealing area (i.e., area of sealing member in contact with the first block and the first charged barrier) compared to gaskets used in conventional suppressors. As such, the force applied per unit area to the first sealing member 32 is significantly higher than those applied to the gaskets for the same applied torque, resulting in the present suppressors having higher pressure resilience. Further, the eluent channel 26 and the first regenerant channel 28 are configured to substantially match with each other in a symmetric fashion. Consequently, the first sealing member 32 can provide even seals around the fluidic pathways in both channels and ensure no fluidic flow outside of these channels. In addition, the eluent channel member 34 and the first block 44 may be made of hard polymer materials. As a result, the eluent channel 26 and the first regenerant channel 28 will not deform or alter under compression or over time while the first sealing member 32 maintains proper seal for the suppressor 20. The materials for making the eluent channel member 34 and the first block 44 need not be the same. These improvements ultimately prolong the life time of the suppressors by providing a good seal and leak free performance and enhance the chromatographic performance including backpressure, noise performance, and peak band dispersion. The suppressor 20 in accordance with the present applicant can be operated continuously at a relatively higher pressure. This feature allows the suppressor of the present invention to be operated in conjunction with other detectors that have an inherently high internal backpressure rating.

Referring still to FIG. 2, the eluent channel member 34, the first charged barrier 30, and the first block 44, each of them may include alignment features 64 in the form of a plurality of holes for facilitating alignment of these components. Holes in one component may be coaxial to holes in another component. One would appreciate that configurations of these holes, including sizes, shapes, locations, number of holes on each component and other configuration parameters can be readily varied. One would also appreciate that configuration of holes in one component is not necessary the same as that in another component.

In various embodiments, the suppressor 20 in accordance with the present application may further include a second regenerant channel 66, a second charged barrier 68 and a second sealing member 70, which may be formed in a similar or substantially the same way as the first regenerant channel 28, the first charged barrier 30 and the first sealing member 32. For example, the second regenerant channel 66 may be formed on a second block 72 that is typically disposed on the other side of the eluent channel member 34 opposite to the first block 44. The second sealing member 70 can be disposed against the second charged barrier 68 for sealing one of the eluent channel member 34 and the second regenerant channel 66. As illustrated in FIG. 2, the second sealing member 70 directly forms the seal to the second regenerant channel 66 and indirectly forms the seal to the eluent channel 26 by urging the second charged barrier 68 against the eluent channel member 34. The second charged barrier 68 may be disposed between the eluent channel member 34 and the second block 72 and separates the eluent channel 26 from the second regenerant channel 66. Like the first sealing member 32, the second sealing member 70 is received in a groove constructed in the second block 72, partially defines the second regenerant channel 66 and provides liquid-tight seal to the eluent channel 26 and the second regenerant channel 66. The second regenerant channel 66 has a regenerant inlet 74 at one end, which may be in fluidic communication with a regenerant reservoir or back pressure coils, and a regenerant outlet 76 at the other end, which may be in fluid communication with waste, eluent generator or other devices. Fittings or other fluidic connectors may be used to assist the fluidic communication. It should be noted that the second charged barrier may have exchangeable ions of the same charge as the first charged barrier or in some applications will have opposite charge to the first charged barrier.

Figure 6A:
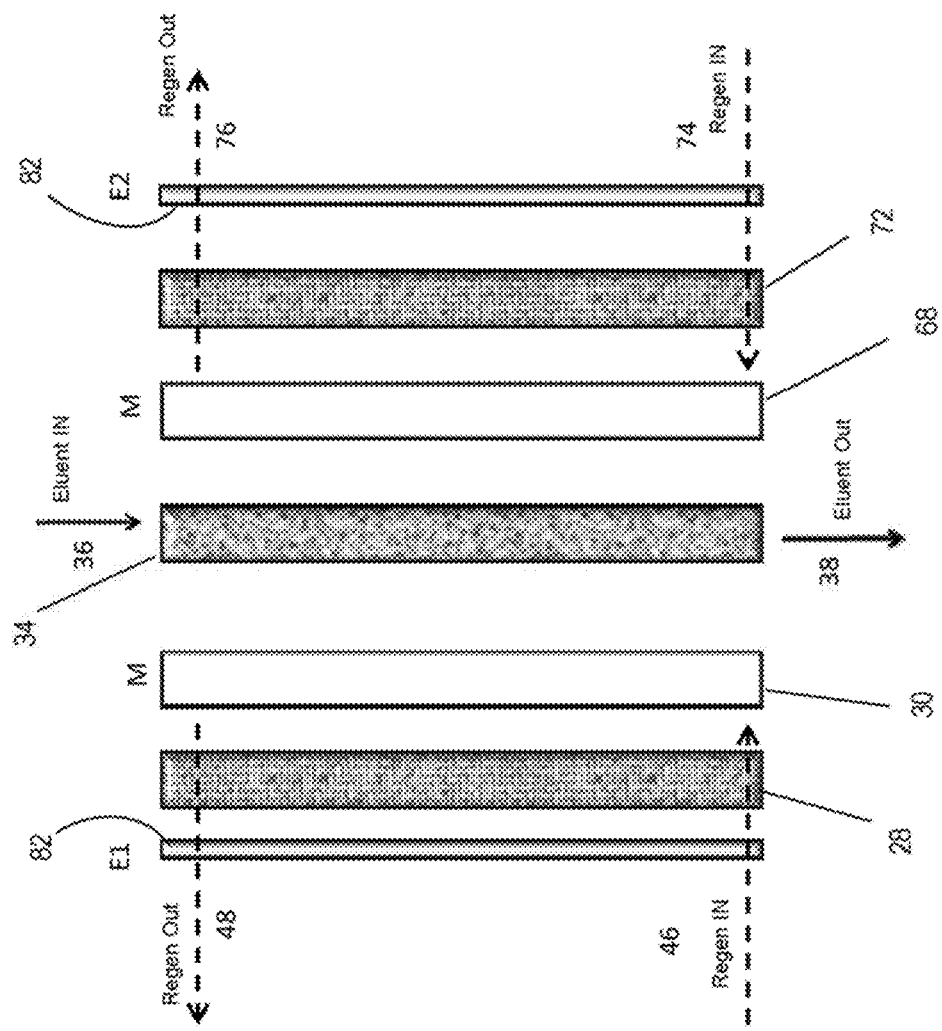
FIG. 6A is a flow diagram of an exemplary suppressor in accordance with the present application.
Figure 6B:
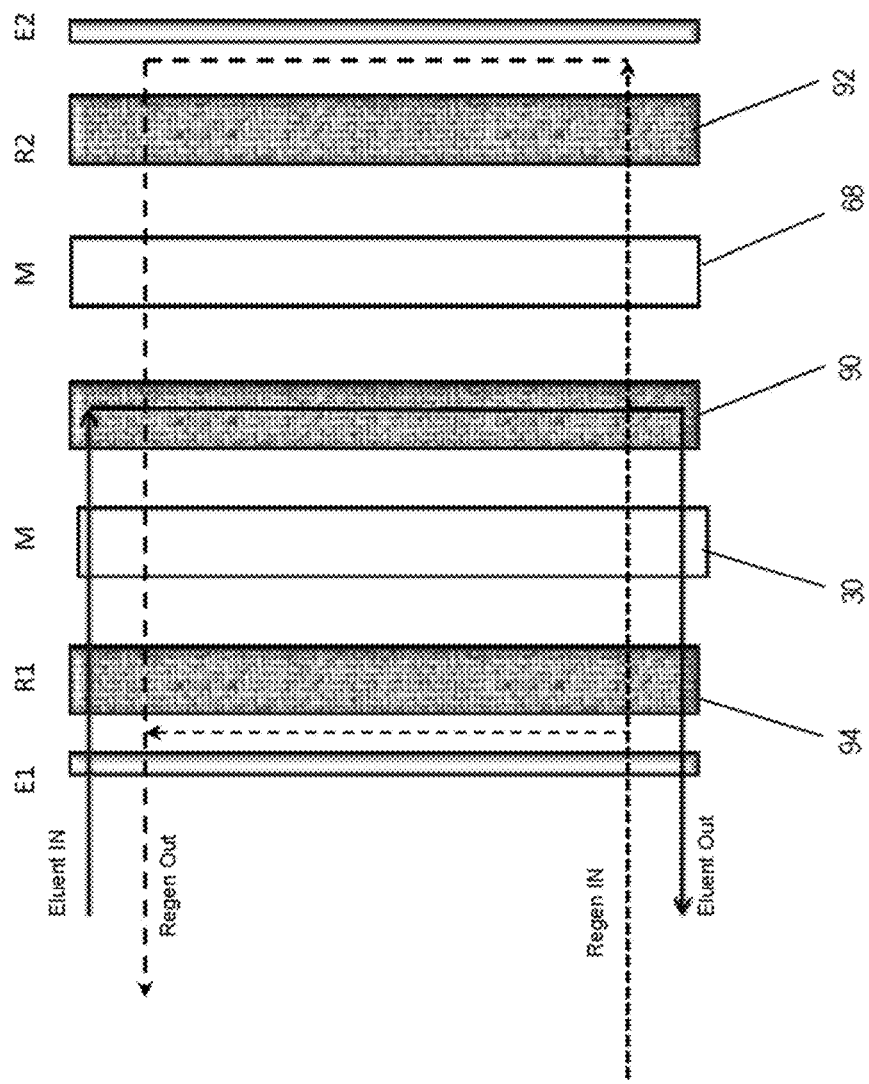
FIG. 6B is a flow diagram of a conventional suppressor

As described above, while the regenerant inlet 46, 74 and outlet 48, 76 are formed in the first block 44 and the second block 72, the eluent inlet 36 and outlet 38 are formed independently in the separated eluent channel member 34. Independent means that the fluidic pathway through the eluent channel does not flow through either the first or the second block. Such configuration allows the formation of independent flow pathways for the eluent and regenerant. A flow diagram corresponding to this configuration is illustrated in FIG. 6A, and a flow diagram corresponding to one of conventional suppressors is illustrated in FIG. 6B for comparison purpose. As shown in FIG. 6B, conventional suppressors route the eluent flow via a couple of through holes in the regenerant channel member 94 and through an eluent channel in a central eluent gasket 90. This imposes the need to align the inlet and outlets of the central eluent gasket with the through holes of the regenerant channel members during assembly and maintain the alignment over time. A slight alignment offset during assembly can result in high backpressure which adversely affects the chromatographic performance of conventional suppressors. In contrast, the eluent inlet 36 and outlet 38 in accordance with the present application are independent from the regenerant inlet 46 and outlet 48 and from the regenerant inlet 74 and outlet 76. Such configuration eliminates the needs for splitting flow or diverting flow via the gaskets as in conventional suppressors. Also, it makes alignment and assembling of suppressors easy and maintains the alignment over time so the eluent can enter and exit the suppressor without any added backpressure.

In various embodiments, the suppressor 20 in accordance with the present application may further include spaced electrodes, such as in the form of flat plates that can be mounted or embedded in the first and/or second blocks. By way of illustration, FIGS. 5B-5C depict an electrode 82 that is mounted on the shelf or ledge 58 in the first block 44 and behind the charged screen 62. In some embodiments, charged screen 62 is free-floating in the regenerant channel. Similarly, another electrode 84 is mounted in the second block 72. The electrodes 82, 84 are formed of highly conductive materials which are inert to the solutions passed through the suppressor. Platinum is a preferred material for this purpose, however, one will appreciate that other suitable materials may be utilized. An electrical potential is applied between the electrodes 82, 84 from any suitable direct current source. Electrical connectors 52, 88 may be used to facilitate electrical communication between the electrodes 82, 84 and a power supply. Upon exceeding a voltage of approximately 1.5 volts, the anode produces hydronium ions and oxygen gas while the cathode produces hydroxide and hydrogen gases from the water splitting reactions. With an electrical potential between the electrodes, a substantially uniform electric field is established across the eluent channel and covers substantially the entire fluidic area, thereby increasing the mobility of ions across the charged barriers. Ultimately, it increases capacity and suppression efficiency and permits regeneration of the suppressors similar to a commercial self regenerating suppressor (SRS). Since the device of the present invention has the eluent channel area matched with the regenerant channel area, a more uniform field and fast regeneration is anticipated in the present design. Regeneration is accomplished by electrolysis generated ions. In some applications a combination of electrolysis and chemical regeneration can also be applied. The electrodes may be omitted in the version of the apparatus for chemical regeneration similar to a commercial micro membrane suppressor (MMS). Optionally or additionally, the suppressor 20 in accordance with the present application may include external support blocks (not shown) that are formed of a rigid material to provide structural support for the remainder of the suppressor 20. In various embodiments, the material is a nonconductive material such as polymethylmethacrylate, however, one will appreciate that various suitable materials such as stainless steel may be utilized. The external support blocks may include appropriate holes for alignment, for accommodating fluidic fittings and/or electrical connectors, and/or for bolts that serve to apply pressure to the components of the suppressor 20 to form liquid-tight seals.

It should be noted that while the above discussions pertain to 2 channel and 3 channel devices the same sealing concept could be applied to multi channel devices in accordance to the present invention.

EXAMPLE 1

Figure 7:
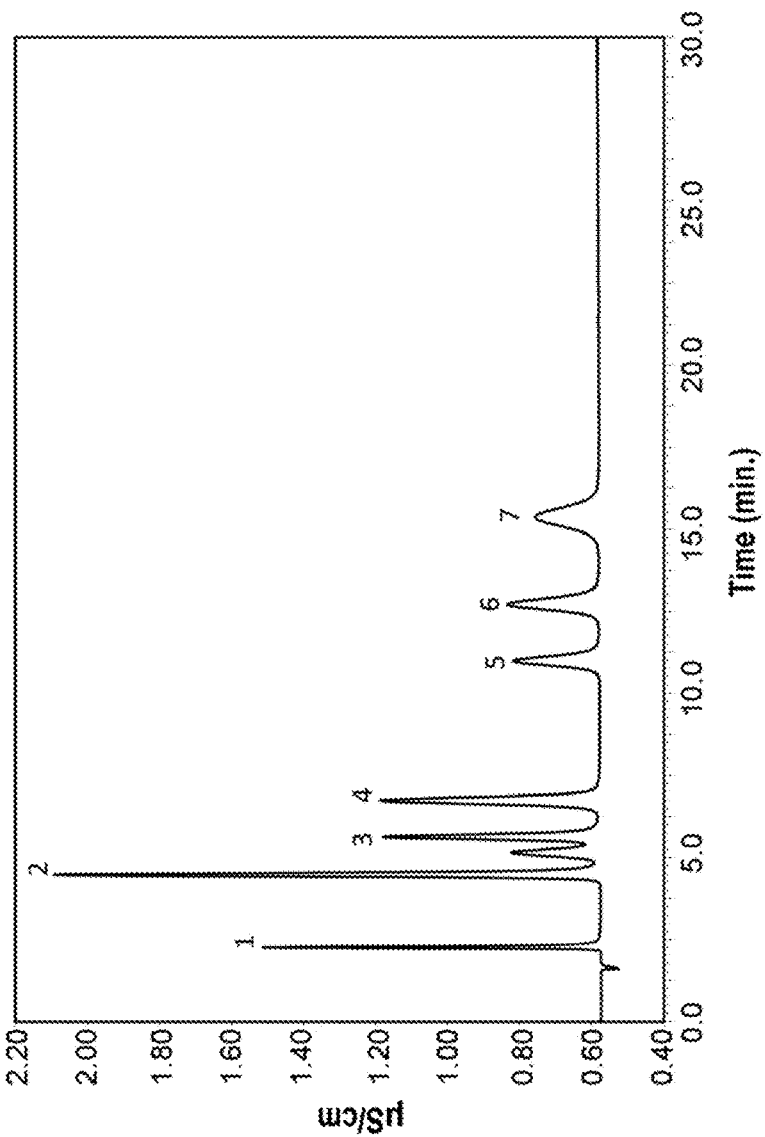
FIG. 7 is a chart of experimental results illustrating use of an exemplary suppressor in accordance with the present application.

In this Example, an exemplary suppressor of FIG. 2 was assembled with cation exchange materials (membrane and screen materials are similar to a commercially available Anion Self-Regenerating Suppressor (ASRS) manufactured by Thermo Scientific, Sunnyvale, Calif.) and using an EPDM "O" ring (32 and 70) and tested for chromatographic performance using an IonPac AS15 column and 38 mM KOH at 1.2 mL/min. The suppressor 20 was powered using a DC power supply at 114 mA. A test mixture comprising of a mixture of 7 anions was analyzed. Fluoride 0.2 ppm (peak 1), Chloride 0.3 ppm (peak 2), Nitrite (peak 3), Bromide (peak 4) and Sulfate (peak 5) at 1 ppm, Nitrate (peak 6) and Phosphate (peak 7) at 1.5 ppm. The chromatogram is shown in FIG. 7.

The suppressor performance was also compared to the performance of a commercially available ASRS (ASRS 300 PN 064554) suppressor that was made with gasketed screen materials in terms of peak efficiency and asymmetry, and the experimental results are shown in a table of FIG. 6. As shown, the suppressor of the present application outperforms the commercially available ASRS 300 suppressor in both categories due to the improved features, specifically the O-ring sealing feature.

EXAMPLE 2

In this Example, the suppressor 20 of the present application was tested with a back pressure of 1000 pounds per square inch (psi) overnight and no leakage was observed. The suppressor performance was maintained even with a backpressure of 1000 psi. The commercially available ASRS 300 suppressor leaked when the pressure exceeded 150 psi during an overnight run. This testing indicated superior leak performance of the suppressor 20 of the present invention. The present suppressor 20 therefore can be easily interfaced with other detectors in series.

EXAMPLE 3

In this Example, the sealing area of the present sealing member (O-ring) was compared with the gasket areas of commercially available SRS 300 suppressors for four different formats. Note that CSRS represents Cation Self-Regenerating Suppressor. The dimension of the ASRS and CSRS refer to the inner diameter of the separation column or more commonly the chromatography format of operation usually designated as standard bore for 4 mm columns and microbore for 2 mm columns. The results tabulated below showed that the gasket areas for the commercially available SRS 300 suppressor are about 4.5 to 6.5 higher than the sealing area of the present sealing member. This means that the applied force per unit area during the torquing and sealing step in the commercially available suppressors is significantly lower than that applied to the sealing member of the present suppressor 20.

| Commercially Available Suppressors | | Present Suppressors 20 |
|---|---|---|
| Type | Gasket Area (Sq. In) | O-ring Area (Sq. In) |
| 2 mm ASRS/CSRS | 4.92 | 0.75 |
| 4 mm CSRS | 3.92 | 0.75 |
| 4 mm ASRS | 3.34 | 0.75 |

EXAMPLE 4

Figure 8:
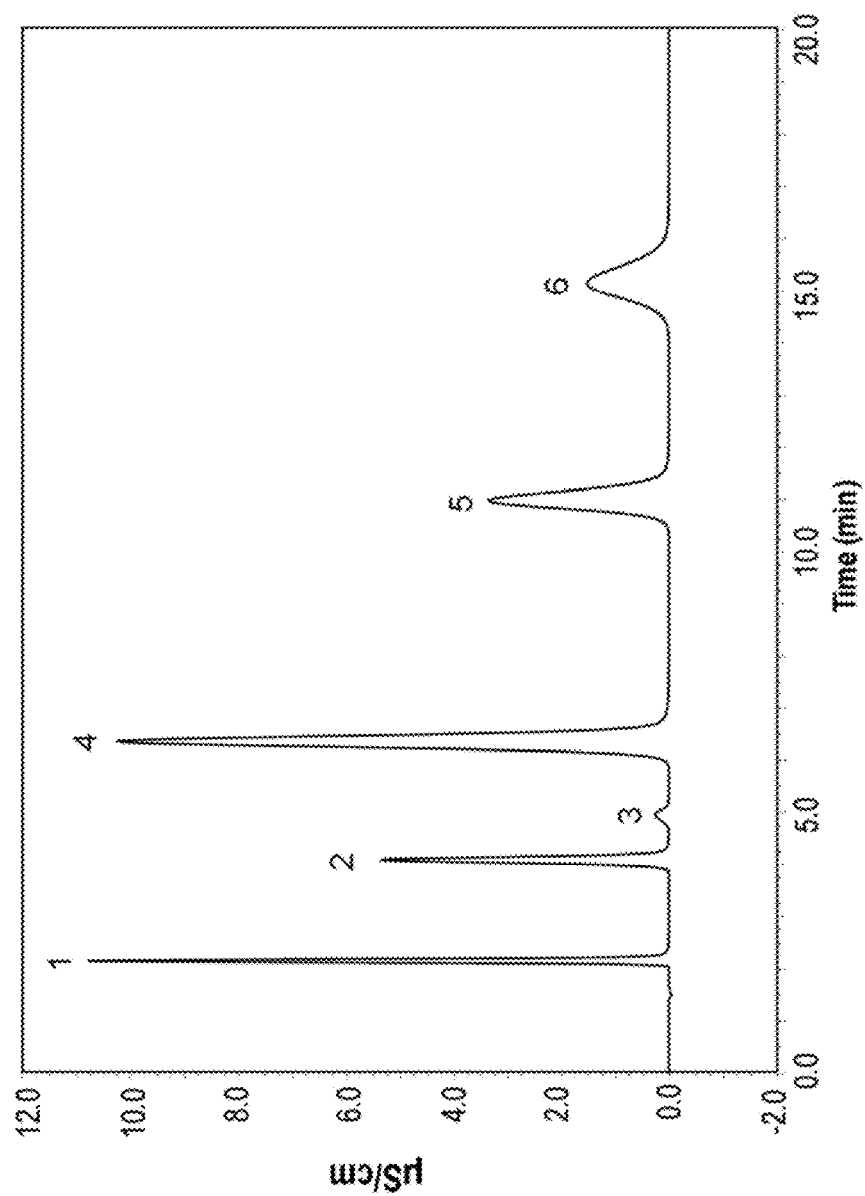
FIG. 8 is an example anion chromatogram obtained with a 4 mm ASRS suppressor assembled in accordance with the present invention.

The suppressor 20 was configured to suppress anions and was tailored for standard bore format of operation. This suppressor 20 was tested with a 25 μL injection of a sample test mixture comprising of five anions namely Fluoride (2 ppm) (peak 1), Chloride (3 ppm) (peak 2), carbonate (peak 3) Sulfate (10 ppm) (peak 4), Nitrate (15 ppm) (peak 5) and Phosphate (15 ppm) (peak 6) as shown in FIG. 8. The column was IonPac AS15 (4×250 mm) that was tested with an eluent concentration of 38 mM KOH at a set temperature of 30° C. and a flow rate of 1.2 mL/min. The current applied to the suppressor was 113 mA. The results indicated good suppression as evidenced by a background of about 1.0 µS/cm and a peak to peak noise of 0.34 nS/cm illustrating excellent performance of the suppressor of the present invention. The chromatogram showing the separation of the five anions with good resolution and peak shape is shown in FIG. 8.

EXAMPLE 5

Figure 9:
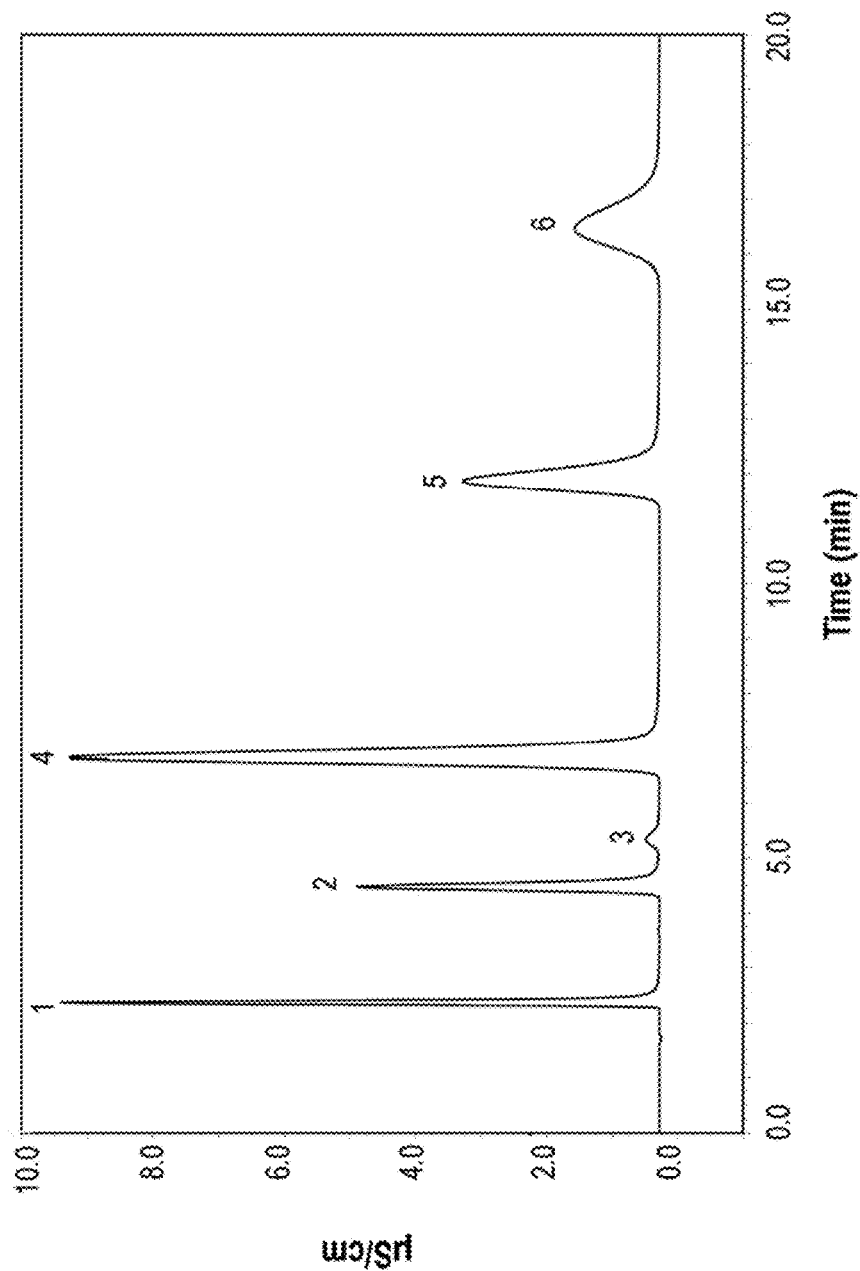
FIG. 9 is an example anion chromatogram obtained with a 2 mm ASRS suppressor assembled in accordance with the present invention

The suppressor 20 was configured to suppress anions and was tailored for microbore format of operation. This suppressor 20 was tested with a 5 µL injection of a sample test mixture comprising of five anions namely Fluoride (2 ppm) (peak 1), Chloride (3 ppm) (peak 2), carbonate (peak 3), Sulfate (10 ppm) (peak 4), Nitrate (15 ppm) (peak 5) and Phosphate (15 ppm) (peak 6) as shown in FIG. 9. The column was IonPac AS15 (2×250 mm) that was tested with an eluent concentration of 38 mM KOH at a set temperature of 30° C. and a flow rate of 0.3 mL/min. The current applied to the suppressor was 29 mA. The results indicated good suppression as evidenced by a background of about 0.27 µS/cm and a peak to peak noise of 0.29 nS/cm illustrating excellent performance of the suppressor of the present invention. The chromatogram showing the separation of the five anions with good resolution and peak shape is shown in FIG. 9.

EXAMPLE 6

Figure 10:
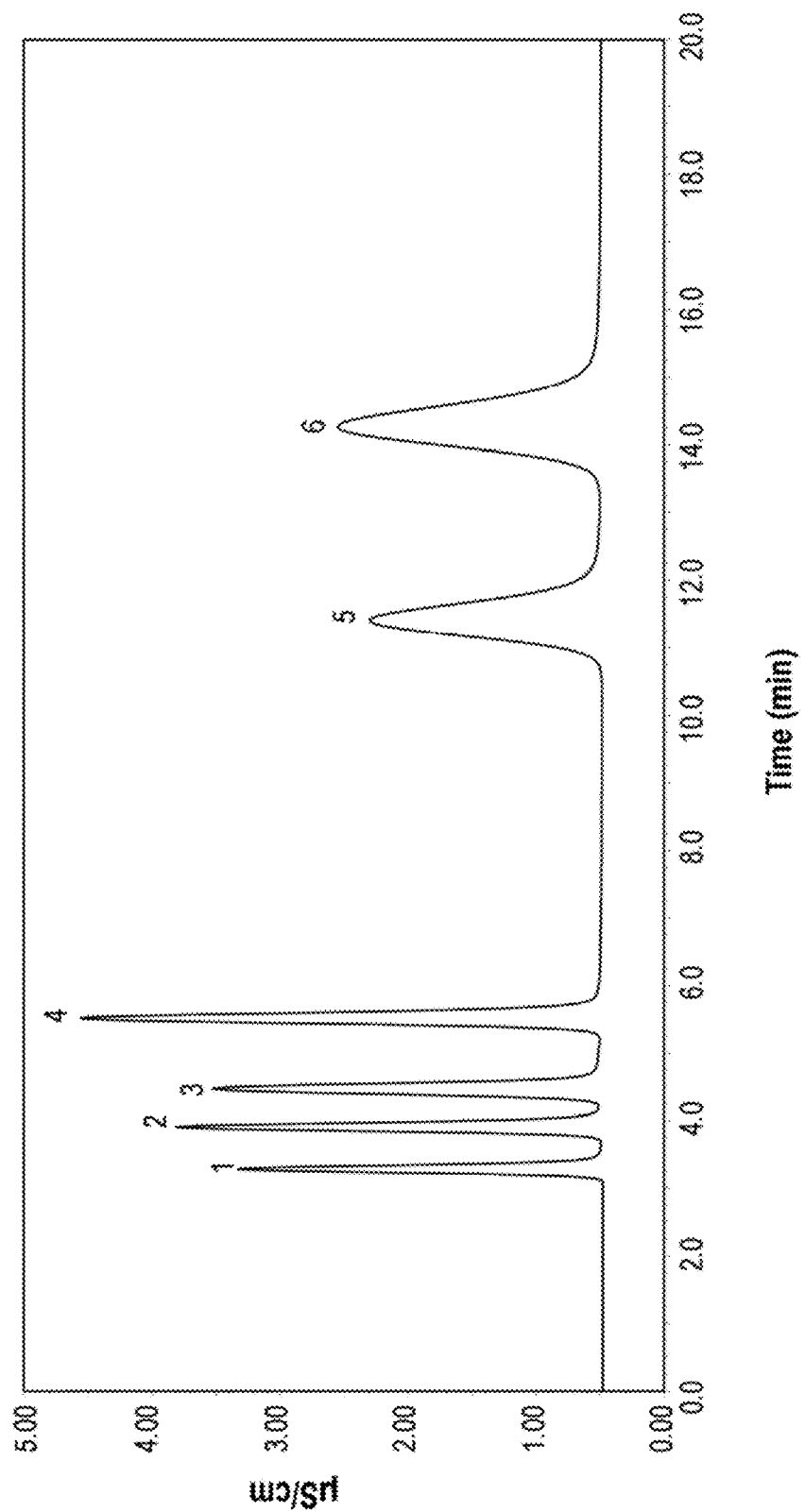
FIG. 10 is an example cation chromatogram obtained with a 4 mm CSRS suppressor assembled in accordance with the present invention.

The suppressor 20 was configured to suppress cations and was tailored for standard bore format of operation. This suppressor 20 was tested with a 25 µL injection of a sample test mixture comprising of six cations namely Lithium (0.5 ppm) (peak 1), Sodium (2 ppm) (peak 2), Ammonium (2.5 ppm) (peak 3), Potassium (5 ppm) (peak 4), Magnesium (2.5 ppm) (peak 5) and Calcium (5 ppm) (peak 6) as shown in FIG. 10. The column was IonPac CS12A (4×250 mm) that was tested with an eluent concentration of 20 mM methanesulfonic acid at a set temperature of 30° C. and a flow rate of 1.0 mL/min. The current applied to the suppressor was 59 mA. The results indicated good suppression as evidenced by a background of about 0.5 µS/cm and a peak to peak noise of 0.12 nS/cm illustrating excellent performance of the suppressor of the present invention. The chromatogram showing the separation of the six cations with good resolution and peak shape is shown in FIG. 10.

EXAMPLE 7

Figures 11A, 11B:
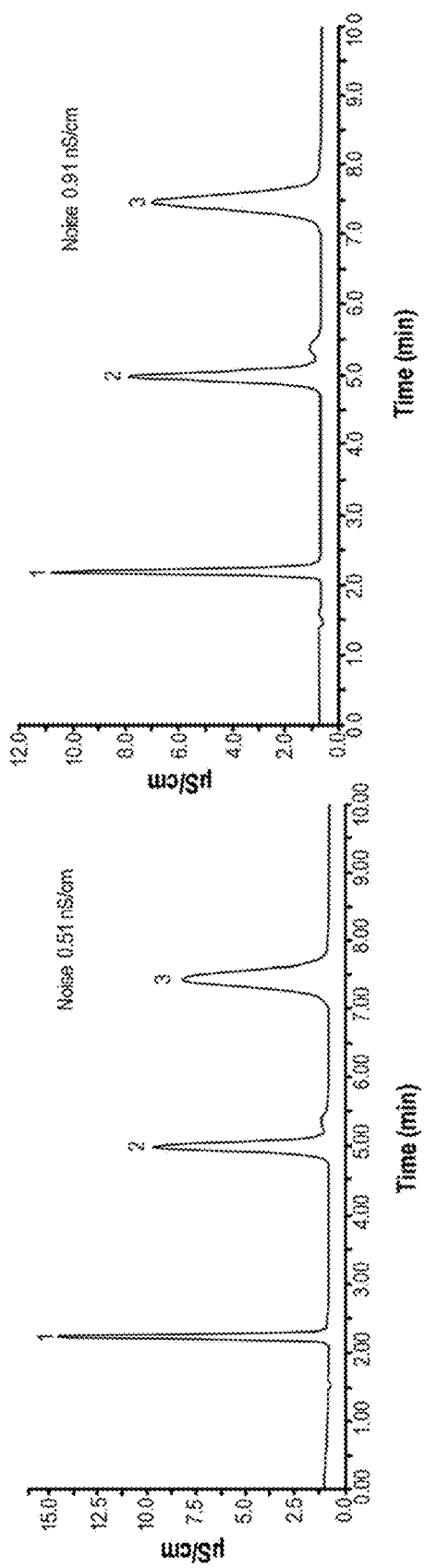
FIGS. 11A-B is a comparison example for anion analysis obtained with a 4 mm ASRS suppressor assembled in accordance with the present invention and a 4 mm ASRS 300 suppressor of the prior art.

The chromatography performance of a suppressor 20 configured to suppress anions and was tailored for standard bore format of operation. This suppressor 20 was compared to the performance of a commercially available 4 mm ASRS 300 suppressor. The suppressor 20 of the present invention (11A) was made with an elastomeric O-ring seal whereas the commercially available suppressor was a commercial product sold by Thermo Scientific called ASRS 300 (11B). The results shown in FIGS. 11A and 11B clearly show superior performance of the suppressor 20 of the present invention in terms of chromatographic efficiency, peak shape as evidenced by good asymmetry numbers, good response values and good noise performance. In particular, the noise performance of the suppressor 20 of the present invention decreased by about a factor of two, which is an important factor in improving the limits of detection for the analyte.

EXAMPLE 8

Figures 12A, 12B:
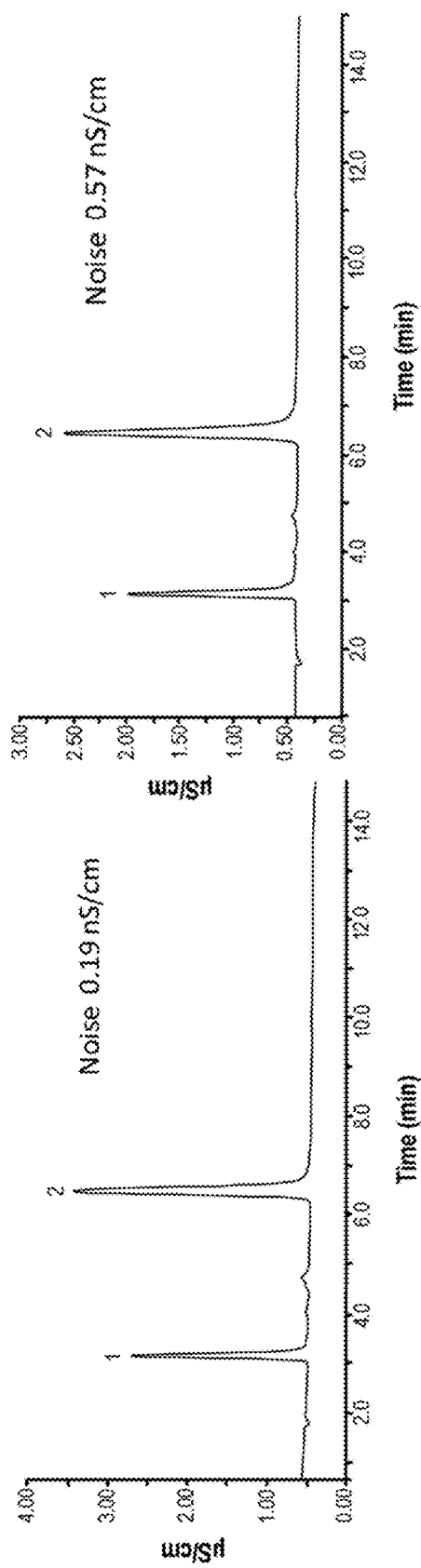
FIGS. 12A-B is a comparison example for cation analysis obtained with a 2 mm CSRS suppressor assembled in accordance with the present invention and a 2 mm CSRS 300 suppressor of the prior art.

The chromatography performance of a suppressor 20 configured to suppress cations and was tailored for a microbore format of operation. This suppressor 20 was compared to the performance of a commercially available 2 mm CSRS 300 suppressor. The suppressor 20 of the present invention (12A) was made with an elastomeric O-ring seal whereas the commercially available suppressor was a commercial product sold by Thermo Scientific called CSRS 300 (12B). The results shown in FIGS. 12A and 12B clearly show superior performance of the suppressor 20 of the present invention in terms of chromatographic efficiency, peak shape as evidenced by good asymmetry numbers, good response values and good noise performance. In particular, the noise performance of the suppressor 20 of the present invention decreased by about a factor of three, which is an important factor in improving the limits of detection for the analyte.

EXAMPLE 9

Figure 13A:
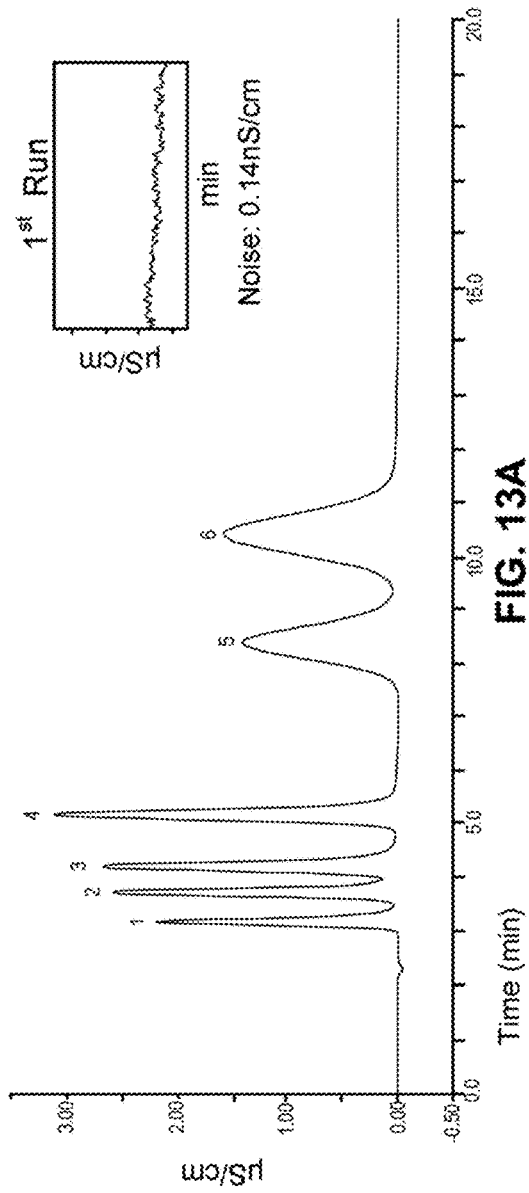
FIGS. 13A-B is a comparison example of the $1^{st}$ run and the $100^{th}$ run for cation analysis obtained with a 2 mm CSRS suppressor assembled in accordance with the present invention.
Figure 13B:
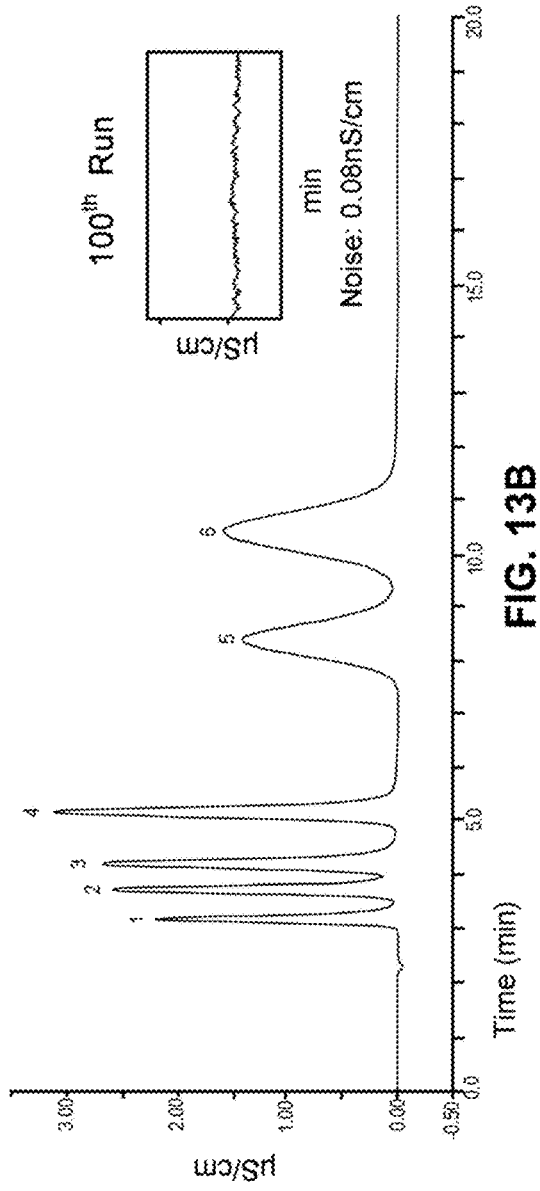

The chromatography performance of a suppressor 20 configured to suppress cations and was tailored for a microbore format of operation. This suppressor 20 was tested for about 100 runs using a 2 mm CS12A column and a comparison was pursued between the $1^{st}$ run (FIG. 13A) and the $100^{th}$ run (FIG. 13B). The results indicated excellent performance of the suppressor 20 of the present invention as evidenced by consistent peaks shapes. The noise performance improved slightly over time as evidenced by a lower background noise observed on the $100^{th}$ run as shown in FIG. 13B.

EXAMPLE 10

Figure 14A:
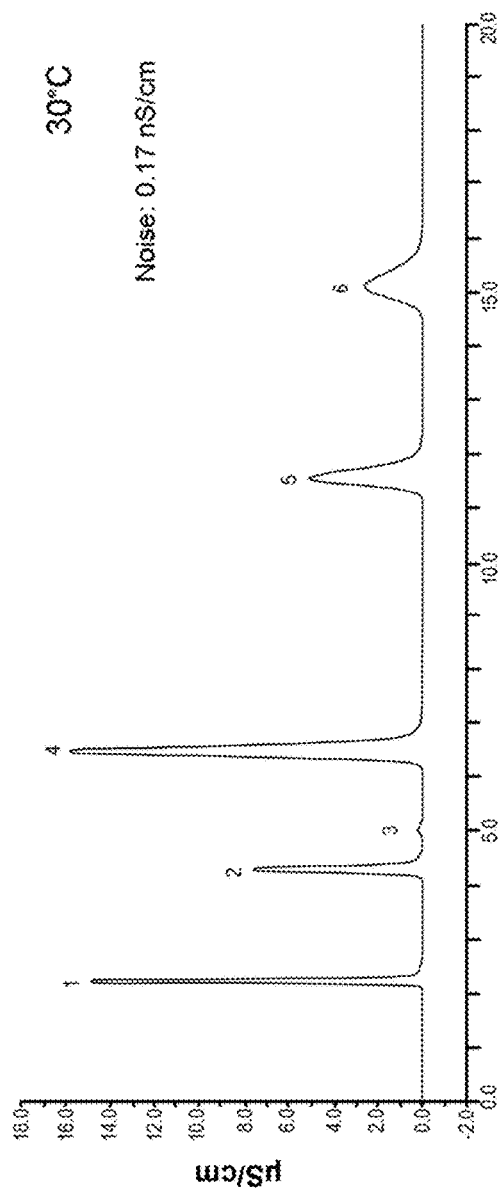
FIGS. 14A-B is a comparison example for anion analysis obtained with a 2 mm ASRS suppressor assembled in accordance with the present invention and tested at column temperature of 30 and 40° C.
Figure 14B:
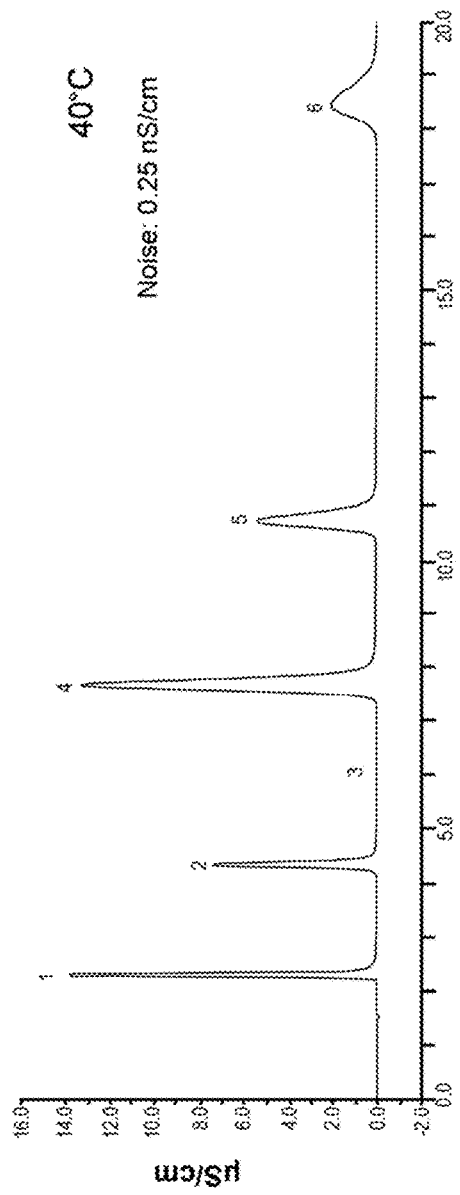

The chromatography performance of a suppressor 20 configured to suppress anions and was tailored for a microbore format of operation. This suppressor 20 was tested at 30° C. (FIG. 14A) or 40° C. (FIG. 14B) using a 2 mm AS15 column. The sample test mixture and elution order in the above figures are similar to Example 5. The results indicated excellent performance of the suppressor of the present invention as evidenced by excellent peak shapes and good noise performance.

EXAMPLE 11

Figure 15A:
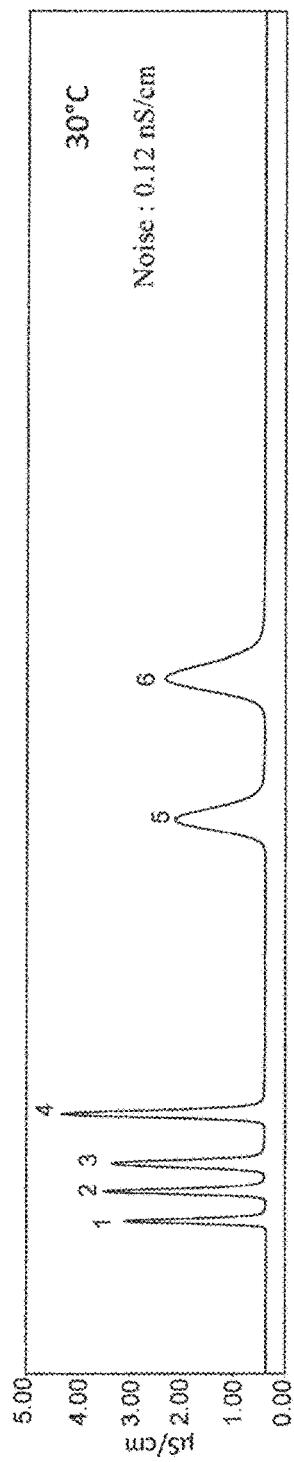
FIGS. 15A-C is a comparison example for cation analysis obtained with a 4 mm CSRS suppressor assembled in accordance with the present invention and tested at column temperatures of 30, 40 and 60° C.
Figure 15B:
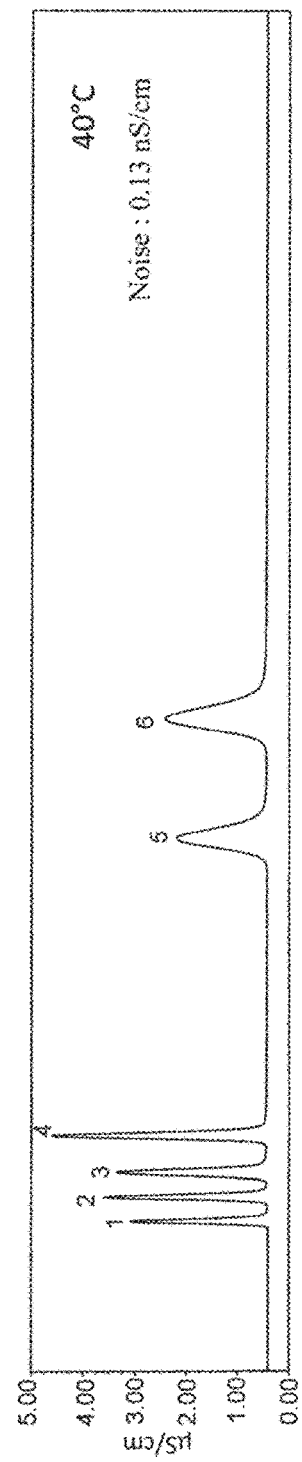
Figure 15C:
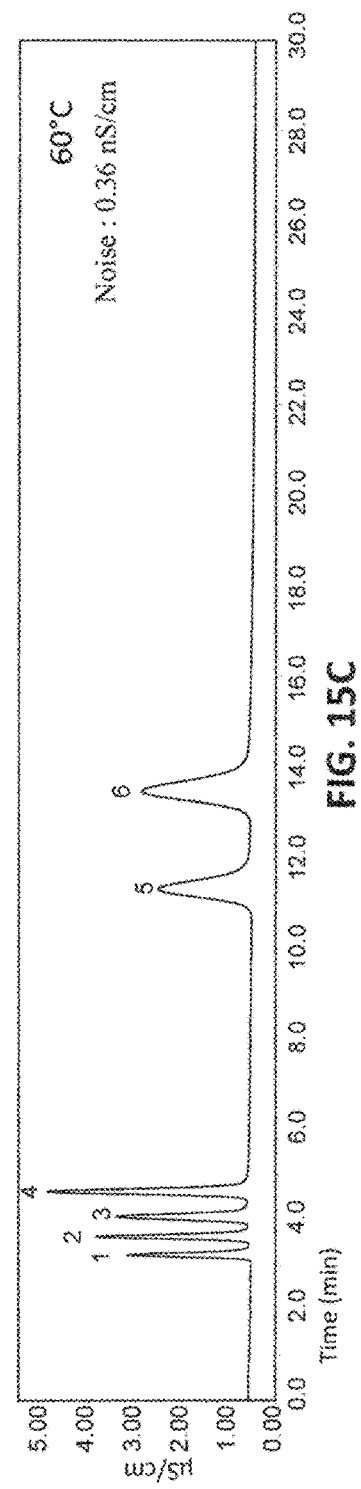

The chromatography performance of a suppressor 20 configured to suppress cations and was tailored for a standard bore format of operation. This suppressor 20 was tested at 30° C. (FIG. 15A), 40° C. (FIG. 15B) and 60° C. (FIG. 15C) using a 4 mm CS12A column. The suppressor 20 was placed inside a chromatographic thermal compartment at the temperatures listed above. The sample test mixture in the above figures and elution order are similar to Example 6. The results indicated excellent performance of the suppressor of the present invention as evidenced by excellent peak shapes and good noise performance. It should be noted that the commercially available CSRS 300 suppressors cannot be operated above 40° C. when placed inside the chromatographic thermal compartment.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of suppressing an eluent, the method comprising:

flowing the eluent into a chromatographic column, in which the eluent contains an ionic species;

directing the eluent from the chromatographic column to a primary channel of a suppressor, the suppressor comprising:

a primary channel member including the primary channel through which the eluent including the ionic species flows, the primary channel extending through the primary channel member;

a first block disposed on a first side of the primary channel member and including a first flat surface that faces the primary channel, a first compartment is defined within the first flat surface;

a first charged barrier having exchangeable ions capable of passing ions of only one charge, positive or negative, and of blocking bulk liquid flow, the first charged barrier disposed between the primary channel member and the first block;

a first O-ring disposed within the first compartment and extending around a periphery of the first compartment, the first O-ring forming a seal with the first charged barrier in an assembled state of the suppressor and thereby defining a peripheral shape of a first regenerant channel between the first charged barrier and the first block, the first regenerant channel extending adjacent to the primary channel;

wherein the first O-ring biases the first charged barrier against the primary channel member in the assembled state of the suppressor thereby forming an indirect seal with a first surface of the primary channel member, a second block disposed on a second side of the primary channel member and including a second flat surface that faces the primary channel, a second compartment is defined within the second flat surface;

a second charged barrier having exchangeable ions capable of passing ions of only one charge, positive or negative, and of blocking bulk liquid flow, the second charged barrier disposed between the primary channel member and the second block; and a second O-ring disposed within the second compartment and extending around a periphery of the second compartment, the second O-ring forming a seal with the second charged barrier in the assembled state of the suppressor and thereby defining a peripheral shape of a second regenerant channel between the second charged barrier and the second block, the second regenerant channel extending adjacent to the primary channel, wherein the second O-ring biases the second charged barrier against the primary channel member in the assembled state of the suppressor thereby forming an indirect seal with a second surface of the primary channel member, the second surface of the primary channel member being opposite to the first surface of the primary channel member, the method further comprising:

flowing a regenerant through the first regenerant channel and the second regenerant channel;

suppressing the eluent in the primary channel by neutralizing the eluent into a weakly ionized form; and detecting the ionic species at a conductivity detector.

2. The method of claim 1, in which the suppressor further comprises a first screen, the first screen disposed within the first regenerant channel.

3. The method of claim 1, in which the primary channel member is formed of polyether ether ketone (PEEK).

4. The method of claim 1, in which the first block and the second block are formed of a polymer.

5. The method of claim 1, in which the first block and the second block are formed of polyether ether ketone (PEEK).

6. The method of claim 1, in which the first sealing member and the second sealing member are each formed of a material selected from the group consisting of ethylene propylene diene monomer (EPDM) rubbers, thermoplastic elastomers, polypropylene, polytetrafluoroethylene (PTFE), and combinations thereof.

7. The method of claim 1, in which the first regenerant channel and the second regenerant channel are configured to have a hexagonal shape.

8. The method of claim 1, in which the first regenerant channel and the second regenerant channel are each configured to include a fluidic area that match a fluidic area of the primary channel.

9. The method of claim 1, in which the directed eluent from the chromatographic column flows through the primary channel in a first direction, and in which the flowed regenerant through the first regenerant channel and the second regenerant channel flows in a second direction that is opposite to the first direction.

10. The method of claim 1, in which the primary channel includes an eluent inlet at one end and with an eluent outlet at the other end thereof;

the first regenerant channel includes a first regenerant inlet at one end and with a first regenerant outlet at the other end thereof; and the second regenerant channel includes a second regenerant inlet at one end and with a second regenerant outlet at the other end thereof, wherein the eluent inlet and the eluent outlet are independent from the first regenerant inlet and the first regenerant outlet and from the second regenerant inlet and the second regenerant outlet.

11. The method of claim 1, in which the suppressor comprises a first electrode and a second electrode disposed in the first regenerant channel and the second regenerant channel, respectively.

12. The method of claim 1, in which the first O-ring directly seals the first regenerant channel and the second O-ring directly seals the second regenerant channel.

13. The method of claim 11 further comprising:

applying an electrical potential between the first electrode and the second electrode, in which the first electrode produces hydronium ions and an oxygen gas and the second electrode produces hydroxide ions and a hydrogen gas.

14. The method of claim 1, in which the primary channel member, the first charged barrier, and the first block include coaxial holes for facilitating alignment of the first charged barrier relative to the regenerant channel.

* * * * *